United States Patent [19]

Tokunaga et al.

[11] Patent Number: 5,401,752

[45] Date of Patent: * Mar. 28, 1995

[54] TETRAHYDROISOQUINOLINE DERIVATIVES, PROCESSES FOR PRODUCING THE SAME AND FUNGICIDES CONTAINING THE SAME

[75] Inventors: Takumi Tokunaga; Teruhiko Ide; Hiroyuki Watanabe; Kenji Tsuzuki; Yasuhito Takasu, all of Shinnanyo, Japan

[73] Assignee: Tosoh Corporation, Yamaguchi, Japan

[*] Notice: The portion of the term of this patent subsequent to Jul. 19, 2011 has been disclaimed.

[21] Appl. No.: 820,732

[22] Filed: Jan. 15, 1992

[30] Foreign Application Priority Data

Jan. 16, 1991 [JP] Japan .................. 3-014945

[51] Int. Cl.$^6$ ............................................ A01N 43/40
[52] U.S. Cl. .................................................... 514/307
[58] Field of Search ........................ 546/144; 514/307

[56] References Cited

FOREIGN PATENT DOCUMENTS 0025598 3/1981 European Pat. Off. ............ 546/144

OTHER PUBLICATIONS

Margni et al, J. Chemical Society, Section C: Organic Chemistry pp. 2578-2580, 1970, Letchworth GB.
Clark, Journal of Organic Chemistry, vol. 52, No. 24, pp. 5378-5382, Nov. 1987, Easton US.
Cushman, Journal of Organic Chemistry, vol. 52, No. 5, pp. 907-915, Mar. 6, 1987.
Haimova et al, Tetrahedron, vol. 33, pp. 31-336, 1977.
Cushman et al, Journal of Organic Chemistry, vol. 42, No. 7, pp. 1111-1116, Apr. 1, 1977.
Clark, Chemical Abstracts, vol. 103, No. 17, abstract No. 141807A, Oct. 28, 1985.
Chemical Abstracts, vol. 23, No, 4, pp. 825-829, 1985.
Atassanoya et al, Chemical Abstracts, vol. 102, No. 11 Abstract No. 95512E, 1985.
Kansal, Chemical Abstracts, vol. 96, No, 13, abstract No. 104563J, Mar. 1982.

Hasigaki et al, Chemical Abstracts, vol. 90, No. 17, abstract No. 137638S, Apr. 1979.
Cushman et al, Total Synthesis of Nitidine Chloride, J. Org. Chem., vol.43, No, 2, pp. 286-288, 1978.
Cushman et al, Total Synthesis of ( )-14-Epicorynoline, Corynoline, and ( )-6-Oxocorynoline, J. Am. Chem. Soc., 105, 2875-2879, 1983.
March, Advanced Organic Chemistry, Third Edition John Wiley & Sons, N.Y., 1985, pp. 1099-1100.

Primary Examiner—Raymond Henley, III
Assistant Examiner—Phyllis G. Spivak
Attorney, Agent, or Firm—Nixon & Vanderhye

[57] ABSTRACT

Tetrahydroisoquinoline derivatives useful as fungicides are disclosed of formula [I]:

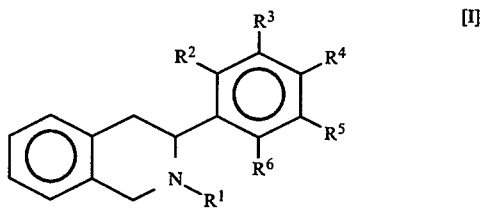

wherein $R^1$ represents $C_1$-$C_5$ linear or branched alkyl, $C_2$-$C_5$ linear or branched alkenyl, $C_2$-$C_5$ linear or branched alkynyl; $R^2$, $R^3$, $R^4$, $R^5$ and $R^6$, the same or different, represent hydrogen, $C_1$-$C_{10}$ linear or branched alkyl, $C_3$-$C_{10}$ linear or branched alkenyl, $C_2$-$C_{10}$ linear or branched alkynyl, $C_1$-$C_{10}$ linear or branched alkoxy, $C_2$-$C_{10}$ linear or branched alkenyloxy, $C_2$-$C_{10}$ linear or branched alkynyloxy, benzyloxy, hydroxy, haloalkyl, amino, mono- or di-substituted amino substituted with $C_1$-$C_4$ linear or branched alkyl, phenyl or halogen; $R^2$ and $R^3$ may be bonded through a group of the formula —O—(CH$_2$-)$_m$O— wherein m represents integer of 1 or 2 or —(CH=CH)$_2$— to form a ring; and $R^4$ and $R^5$ may be bonded through a group of the formula —O—(CH$_2$-)$_m$O— wherein m represents an integer of 1 or 2 or —(CH=CH)$_2$— to form a ring.

3 Claims, No Drawings

TETRAHYDROISOQUINOLINE DERIVATIVES, PROCESSES FOR PRODUCING THE SAME AND FUNGICIDES CONTAINING THE SAME

BACKGROUND OF THE INVENTION

I. Field of the Invention

The present invention relates to novel tetrahydroisoquinoline derivatives, processes of producing the same and fungicides containing the same as active ingredients.

II. Description of the Related Art

Fungicides are indispensable in agriculture to prevent plant diseases and to increase the yield of the agricultural products. A number of agricultural fungicides are now used. However, some of them have poor fungicidal activities and some of them have restrictions on their use because of their toxicities to environment. Further, when the same or similar fungicides are used for a long time, pathogenic plant fungi which are resistant to the fungicides are generated, so that the effects of the fungicides are reduced. Thus, a fungicide with sufficient fungicidal activity, which is free from the problems on the pollution of environment and on the emergence of drug-resistant fungi is demanded.

Tetrahydroisoquinoline skeleton is contained in the benzophenanetrizine alkaloids and various physiological activities thereof including anti-cancer activity are known (e.g., J. Am. Chem. Soc. 1983, 105, 2873; J. Org. Chem. 1978, 43, 286). However, the present inventors found novel tetrahydroisoquinoline derivatives having fungicidal activities.

SUMMARY OF THE INVENTION

Accordingly, an object of the present invention is to provide a novel compound effective as a fungicide with sufficient fungicidal activity and which is free from the problems on the pollution of environment and on the emergence of drug-resistant fungi.

The present inventors intensively studied to discover novel tetrahydroisoquinoline derivatives and that these tetrahydroisoquinoline derivatives have high fungicidal activities and have substantially no phytotoxicity against useful plants, thereby completing the present invention.

That is, the present invention provides a tetrahydroisoquinoline derivative of the formula [I] and acid addition salts thereof:

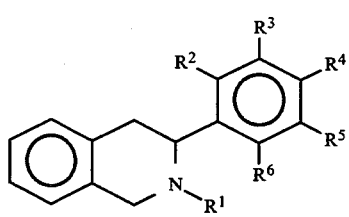

(wherein $R^1$ represents $C_1$–$C_5$ linear or branched alkyl, $C_2$–$C_5$ linear or branched alkenyl, $C_2$–$C_5$ linear or branched alkynyl; $R^2$ $R^3$ $R^4$ $R^5$ and $R^6$ the same or different, represent hydrogen, $C_1$–$C_{10}$ linear or branched, alkyl, $C_3$–$C_{10}$ linear or branched alkenyl, $C_2$–$C_{10}$ linear or branched alkynyl, $C_1$–$C_{10}$ linear or branched alkoxy, $C_2$–$C_{10}$ linear or branched alkenyloxy, $C_2$–$C_{10}$ linear or branched alkynyloxy, benzyloxy, hydroxy, haloalkyl, amino, mono- or di-substituted amino substituted with $C_1$–$C_4$ linear or branched alkyl, phenyl or halogen; $R^2$ and $R^3$ may be bonded through a group of the formula $-(O-CH_2)_m O-$ (wherein m represents an integer of 1 or 2) or $-(CH=CH)_2-$ to form a ring; and $R^4$ and $R^5$ may be bonded through a group of the formula $-O-(CH_2)_m O-$ (wherein m represents an integer of 1 or 2) or $-(CH=CH)_2-$ to form a ring.

The present invention also provides a tetrahydroisoquinoline derivative of the formula [III]:

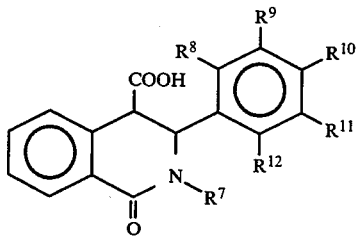

(wherein $R^7$ represents $C_1$–$C_5$ linear or branched alkyl, $C_2$–$C_5$ linear or branched alkenyl or $C_2$–$C_5$ linear or branched alkynyl; $R^8$ $R^9$ $R^{10}$ $R^{11}$ and $R^{12}$ the same or different, represent hydrogen, $C_1$–$C_{10}$ linear or branched alkyl, $C_3$–$C_{10}$ linear or branched alkenyl, $C_2$–$C_{10}$ linear or branched alkynyl, $C_1$–$C_{10}$ linear or branched alkoxy, $C_2$–$C_{10}$ linear or branched alkenyloxy, $C_2$–$C_{10}$ linear or branched alkynyloxy, benzyloxy, hydroxy, haloalkyl, amino, mono- or di-substituted amino substituted with $C_1$–$C_4$ linear or branched alkyl, phenyl or halogen, alkoxycarbonyloxy of the formula

(wherein $R^{13}$ represents $C_1$–$C_{10}$ linear or branched alkyl), or carbamoyloxy of the formula

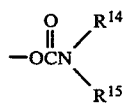

(wherein $R^{14}$ and $R^{15}$ the same or different, represent hydrogen or $C_1$–$C_{10}$ linear or branched alkyl); $R^8$ and $R^9$ may be bonded through a group of the formula $-(O-CH_2)_m O-$ (wherein m represents an integer of 1 or 2) or $-(CH=CH)_2-$ to form a ring, and $R^{10}$ and $R^{11}$ may be bonded through a group of the formula $-O-(CH_2)_m O-$ (wherein m represents an integer of 1 or 2) or $-(CH=CH)_2-$ to form a ring.

The present invention further provides a tetrahydroisoquinoline derivative of the formula [IV]:

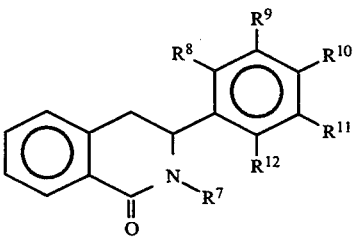

wherein $R^7$, $R^8$, $R^9$, $R^{10}$, $R^{11}$ and $R^{12}$ represent the same meanings as in the formula [III]).

The present invention still further provides fungicides comprising as active ingredients the above-mentioned tetrahydroisoquinoline derivatives according to the present invention.

By the present invention, novel tetrahydroisoquinoline derivatives useful as fungicides with sufficient fungicidal activities and which are free from the problems on the pollution of environment and on the emergence of drug-resistant fungi were provided.

DETAILED DESCRIPTION OF THE PREFERRED EMBODIMENTS

According to a first aspect of the present invention, the tetrahydroisoquinoline derivative of the above-described formula [I] is provided. In the formula [I], $R^1$ represents $C_1$-$C_5$ linear or branched alkyl such as methyl, ethyl, propyl, isopropyl, butyl, isobutyl, sec-butyl, tert-butyl, pentyl, isopentyl, neopentyl and tert-pentyl; $C_2$-$C_5$ linear or branched alkenyl such as vinyl, allyl, isopropenyl, 1-propenyl, 1-methyl-1-propenyl, 2-methyl-1-propenyl, 1-methyl-2-propenyl, 2-butenyl, 1-methyl-2-butenyl, 2-methyl-2-butenyl, 3-methyl-2-butenyl, 1,1-dimethyl-2-propenyl; or $C_2$-$C_5$ linear or branched alkynyl such as 2-propynyl, 1-methyl-2-propynyl and 1,1-dimethyl-2-propynyl.

In the formula [I], $R^2$, $R^3$, $R^4$, $R^5$ and $R^6$, the same or different, represent hydrogen atom; $C_1$-$C_{10}$ linear or branched alkyl such as methyl, ethyl, propyl, isopropyl, butyl, isobutyl, sec-butyl, tert-butyl, pentyl, isopentyl, neopentyl, tert-pentyl, hexyl, isohexyl, 3-methylpentyl, 2-methylpentyl, 1-methylpentyl, 3-ethylbutyl, 2-ethylbutyl, 1-ethylbutyl, 1,1,2-trimethylpropyl, 2-propylpropyl, 1-propylpropyl, 1,1-dimethylbutyl, 1-ethyl-1-methylpropyl, 1,1,2,2-tetramethylpropyl, 1,1,2-trimethylbutyl, 1,1-dimethylpentyl, 1,1,2,2-tetramethylpentyl or 1-ethyl-1-methylpentyl; $C_3$-$C_{10}$ linear or branched alkenyl such as isopropenyl, 1-propenyl, 2-propenyl, 1-ethylvinyl, 1-methyl-1-propenyl, 2-methyl-1-propenyl, 1-methyl-2propenyl, 2-methyl-2-propenyl, 1-butenyl, 2-butenyl, 3-butenyl, 1,1-dimethyl-2-propenyl, 1-methyl-2-butenyl, 2-methyl-2-butenyl, 3-methyl-2-butenyl, 1,1-dimethyl-2-butenyl, 1,1-dimethyl-3-butenyl, 1,1,2-trimethyl-2-butenyl, 1,1,2-trimethyl-3-butenyl or 1,1,2,2-tetramethyl-3-butenyl; $C_2$-$C_{10}$ linear or branched alkynyl such as ethynyl, 1-propynyl, 2-propynyl, 1-methyl-2-propynyl, 1,1-dimethyl-2-propynyl, 2-butynyl, 1-methyl-2-butynyl, 1,1-dimethyl-2-butynyl, 1,1-dimethyl-3-butynyl, 1,1,2-trimethyl-3-butynyl or 1,1,2,2-tetramethyl-3-butynyl; $C_1$-$C_{10}$ linear or branched alkoxy such as methoxy, ethoxy, propoxy, isopropoxy, butoxy, isobutoxy, sec-butoxy, tert-butoxy, pentyloxy, isopentyloxy, neopentyloxy, tert-pentyloxy, hexyloxy, isohexyloxy, 3-methylpentyloxy, 2-methylpentyloxy, 1-methylpentyloxy, 3-ethylbutyloxy, 2-ethylbutyloxy, 1-ethylbutyloxy, 2-propylpropyloxy and 1-propylpropyloxy; $C_2$-$C_{10}$ linear or branched alkenyloxy such as vinyloxy, allyloxy, isopropenyloxy, 1-propenyloxy, 1-methyl-1-propenyloxy, 2-methyl-1-propenyloxy, 1-methyl-2-propenyloxy, 2-butenyloxy, 1-methyl-2-butenyloxy, 2-methyl-2-butenyloxy, 3-methyl-2-butenyloxy or 1,1-dimethyl-2-propenyloxy; $C_2$-$C_{10}$ linear or branched alkynyloxy such as ethynyloxy, 1-propynyloxy, 2-propynyloxy, 1-methyl-2-propynyloxy or 1,1-dimethyl-2-propynyloxy; benzyloxy; hydroxy; haloalkyl such as trifluoromethyl; amino; mono- or di-substituted amino substituted with $C_1$-$C_4$ linear or branched alkyl, such as methylamino, ethylamino, dimethylamino, propylamino, N-ethyl-N-methylamino, isopropylamino, N-isopropyl-N-methylamino, butylamino, N-butyl-N-methylamino or isobutylamino; phenyl; or halogen atom such as fluorine, chlorine, bromine or iodine.

In the formula [I] $R^2$ and $R^3$ and/or $R^4$ and $R^5$ may be bonded through a group of the formula —O—CH$_2$-)$_m$O— (wherein m represents an integer of 1 or 2) or —CH=CH)$_2$ to form a ring. Examples of such substituents on the 3-position of the isoquinoline ring include 3,4-methylenedioxyphenyl, 1-naphthyl and 2-naphthyl.

Examples of the acid addition salts of the tetrahydroisoquinoline derivative of the formula [I] includes agriculturally acceptable acid addition salts such as hydrogen chloride salt, hydrogen bromide salt, sulfuric acid salt, nitric acid salt, acetic acid salt, oxalic acid salt, tartaric acid salt, benzene sulfonic acid salt and methane sulfonic acid salt.

The tetrahydroisoquinoline derivative represented by the formula [I] may preferably be produced by reducing a lactam derivative of the formula [II]:

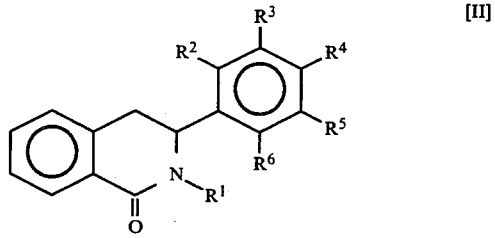

(wherein $R^1$, $R^2$, $R^3$, $R^4$, $R^5$ and $R^6$ represent the same meanings as in the formula [I])
with a hydrogenating agent in a solvent at $-10°$ C. to $200°$ C., preferably $0°$ C. to $130°$ C. for several minutes to several days.

Preferred examples of the hydrogenating agent which may be employed in the above-described reaction include lithium aluminum hydride, diborane, sodium borohydride, lithium borohydride and sodium bis(2-methoxyethoxy)aluminum hydride. The amount of the hydrogenating agent may preferably be 0.2 to 20 equivalents with respect to one equivalent of the lactam derivative of the formula [II].

Preferred examples of the solvents which may be employed include ethers such as ethyl ether, tetrahydrofuran, dioxane and bis(2-methoxyethyl)ether; tertiary amines such as pyridine and triethylamine; aromatic hydrocarbons such as benzene, toluene and xylene; alcohols such as methanol.

The lactam derivative of the formula [II] may preferably be produced according to the following reaction equation [i]:

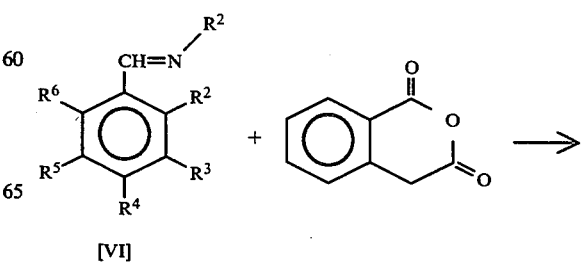

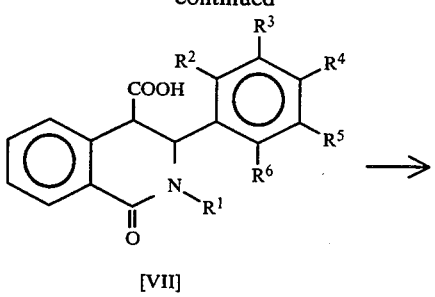

[VII]

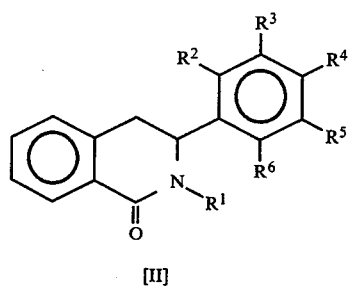

[II]

In the reaction equation [i], $R^1$, $R^2$, $R^3$, $R^4$, $R^5$ and $R^6$ represent the same meanings as mentioned above.

In the reaction equation [i], the tetrahydroisoquinoline derivative of the formula [VII] may preferably be produced by reacting the imine derivative of the formula [VI] with homophthalic anhydride in a solvent at $-10°$ C. to $200°$ C., preferably $0°$ C. to $100°$ C. for 5 minutes to 200 hours, preferably 30 minutes to 60 hours.

The amount of the homophthalic anhydride may preferably be 0.1 equivalent to 10 equivalents per one equivalent of the imine derivative of the formula [VI].

Although the reaction may be carried out without using a solvent, the reaction is usually carried out in the presence of a solvent. Preferred examples of the solvent include nitriles such as acetonitrile and propionitrile; ethers such as ethyl ether, tetrahydrofuran, dioxane and bis(2-methoxyethyl) ether; aromatic hydrocarbons such as benzene, toluene and xylene.

The lactam derivative of the formula [II] may preferably be produced by treating the tetrahydroisoquinoline derivative of the formula [VII] in a solvent in the presence of a base at $60°$ C. to $250°$ C., preferably $100°$ C. to $200°$ C. for 5 minutes to 200 hours, preferably 30 minutes to 60 hours.

Preferred examples of the base employed in this reaction include carbonates and hydrogen carbonates of alkaline metals such as sodium carbonate, potassium carbonate, sodium hydrogen carbonate and potassium hydrogen carbonate. The amount of the base may preferably be 0.1–10 equivalents per one equivalent of the tetrahydroisoquinoline derivative of the formula [VII].

Preferred examples of the solvent which may be employed in this reaction include aromatic hydrocarbons such as toluene and xylene; ethers such as dioxane; and polar solvents such as N,N-dimethylformamide (DMF), dimethylsulfoxide (DMSO), 1,3-dimethyl-2-imidazolidinone, hexamethylphosphoric triamide (HMPA).

According to a second aspect of the present invention, tetrahydroisoquinoline derivatives of the above-described formulae [III] and [IV] are provided.

In the formulae [III] and [IV], $R^7$ represents $C_1$–$C_5$ linear or branched alkyl such as methyl, ethyl, propyl, isopropyl, butyl, isobutyl, sec-butyl, tert-butyl, pentyl, isopentyl, neopentyl and tert-pentyl; $C_2$–$C_5$ linear or branched alkenyl such as vinyl, allyl, isopropenyl, 1-propenyl, 1-methyl-1-propenyl, 2-methyl-1-propenyl, 1-methyl-2-propenyl, 2-butenyl, 1-methyl-2-butenyl, 2-methyl-2-butenyl, 3-methyl-2-butenyl, 1,1-dimethyl-2-propenyl; or $C_2$–$C_5$ linear or branched alkynyl such as 2-propynyl, 1-methyl-2-propynyl or 1,1-dimethyl-2-propynyl.

In the formulae [III] and [IV], $R^8$, $R^9$, $R^{10}$, $R^{11}$ and $R^{12}$, the same or different, represent hydrogen atom; $C_1$–$C_{10}$ linear or branched alkyl such as methyl, ethyl, propyl, isopropyl, butyl, isobutyl, sec-butyl, tert-butyl, pentyl, isopentyl, neopentyl, tert-pentyl, hexyl, isohexyl, 3-methylpentyl, 2-methylpentyl, 1-methylpentyl, 3-ethylbutyl, 2-ethylbutyl, 1-ethylbutyl, 1,1,2-trimethylpropyl, 2-propylpropyl, 1-propylpropyl, 1,1-dimethylbutyl, 1-ethyl-methylpropyl, 1,1,2,2-tetramethylpentyl or 1-ethyl-1-methylpentyl; $C_3$–$C_{10}$ linear or branched alkenyl such as isopropenyl, 1-propenyl, 2-propenyl, 1-ethylvinyl, 1-methyl-1-propenyl, 2-methyl-1-propenyl, 1-methyl-2-propenyl, 2-methyl-2-propenyl, 1-butenyl, 2-butenyl, 3-butenyl, 1,1-dimethyl-2-propenyl, 1-methyl-2-butenyl, 2-methyl-2-butenyl, 3-methyl-2-butenyl, 1,1-dimethyl-2-butenyl, 1,1,2-trimethyl-3-butenyl, 1,1,2-trimethyl-2-butenyl, 1,1-dimethyl-3-butenyl, 1,1,2-trimethyl-2-butenyl, 1,1,2-trimethyl-3-butenyl or 1,1,2,2-tetramethyl-3-butenyl; $C_2$–$C_{10}$ linear or branched alkynyl such as ethynyl, 1-propynyl, 2-propynyl, 1-methyl-2-propynyl, 1,1-dimethyl-2-propynyl, 2-butynyl, 1-methyl-2-butynyl, 1,1-dimethyl-2-butynyl, 1,1-dimethyl-3-butynyl, 1,1,2-trimethyl-3-butynyl or 1,1,2,2-tetramethyl-3-butynyl; $C_1$–$C_{10}$ linear or branched alkoxy such as methoxy, ethoxy, propoxy, isopropoxy, butoxy, isobutoxy, sec-butoxy, tert-butoxy, pentyloxy, isopentyloxy, neopentyloxy, tert-pentyloxy, hexyloxy, isohexyloxy, 3-methylpentyloxy, 2-methylpentyloxy, 1-methylpentyloxy, 3-ethylbutyloxy, 2-ethylbutyloxy, 1-ethylbutyloxy, 2-propylpropyloxy or 1-propylpropyloxy; $C_2$–$C_{10}$ linear or branched alkenyloxy such as vinyloxy, allyloxy, isopropenyloxy, 1-propenyloxy, 1-methyl-1-propenyloxy, 2-methyl-1-propenyloxy, 1-methyl-2-propenyloxy, 2-butenyloxy, 1-methyl-2-butenyloxy, 2-methyl-2-butenyloxy, 3-methyl-2-butenyloxy or 1,1-dimethyl-2-propenyloxy; $C_2$–$C_{10}$ linear or branched alkynyloxy such as ethynyloxy, 1-propynyloxy, 2-propynyloxy, 1-methyl-2-propynyloxy or 1,1-dimethyl-2propynyloxy; benzyloxy; hydroxy; haloalkyl such as trifluoromethyl; amino; mono- or di-substituted amino substituted with $C_1$–$C_4$ linear or branched alkyl such as methylamino, ethylamino, dimethylamino, propylamino, N-ethyl-N-methylamino, isopropylamino, N-isopropyl-N-methylamino, butylamino, N-butyl-N-methylamino or isobutylamino; phenyl; halogen atom such as fluorine, chlorine, bromine or iodine; alkoxycarbonyloxy of the formula

(wherein $R^{13}$ represents $C_1$–$C_{10}$ linear or branched alkyl)
such as methoxycarbonyloxy or ethoxycarbonyloxy; or carbamoyloxy of the formula

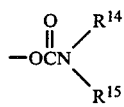

(wherein $R^{14}$ and $R^{15}$ the same or different represent hydrogen or $C_1$-$C_{10}$ linear or branched alkyl) such as N,N-dimethylcarbamoyloxy or N-ethyl-N-methylcarbamoyloxy.

In the formulae [III] and [IV], $R^8$ and $R^9$, and/or $R^{10}$ and $R^{11}$ may be bonded through a group of the formula —O$\pm$CH$_2)_{\overline{m}}$O— (wherein m represents an integer of 1 or 2) or —CH=CH$)_{\overline{2}}$ to form a ring. Examples of such substituents on the 3-position of the isoquinoline ring include 3,4-methylenedioxyphenyl, 1-naphthyl and 2-naphthyl.

The tetrahydroisoquinoline derivative of the formula [III] may preferably be produced by reacting an imine derivative of the formula [V]:

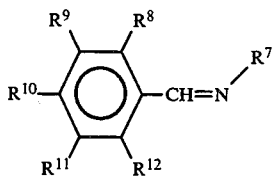

with homophthalic anhydride in the absence or presence of a solvent at −10° C. to 200° C., preferably 0° C. to 100° C. for 5 minutes to 200 hours, preferably 30 minutes to 60 hours.

The amount of the homophthalic anhydride employed in this reaction may preferably be 0.1 to 10 equivalents per one equivalent of the imine derivative of the formula [V].

Although this reaction may be carried out in the absence of a solvent, the reaction may usually be carried out in the presence of a solvent. Preferred examples of the solvent include nitriles such as acetonitrile and propionitrile; ethers such as ethyl ether, tetrahydrofuran, dioxane and bis(2-methoxyethyl)ether; and aromatic hydrocarbons such as benzene, toluene and xylene.

Since the tetrahydroisoquinoline derivative of the formula [III] has two asymmetric carbon atoms, there are four stereoisomers, and these stereoisomers constitute two pairs of enantiomers. The pairs of enantiomers may be separated into each pair of enantiomers by the conventional column chromatography or recrystallization.

In the pair of enantiomers in which the methine hydrogen on the 4-position of the isoquinoline ring emerges in the side of lower magnetic field in $^1$H-NMR spectrum (in DMSO-d$_6$ solvent), the coupling constant between the methine hydrogen on the 4-position and the methine hydrogen on the 3-position of the isoquinoline ring is J=6 Hz, so that these isomers are assumed to have cis form (J. Org. Chem. 1978, 43, 286). This pair of enantiomers is herein after referred to as "cis compound".

In the pair of enantiomers in which the methine hydrogen on the 4-position of the isoquinoline ring emerges in the side of higher magnetic field in $^1$H-NMR spectrum (in DMSO-d$_6$ solvent), the coupling constant between the methine hydrogen on the 4-position and the methine hydrogen on the 3-position of the isoquinoline ring is J=0 Hz, so that these isomers are assumed to have trans form (J. Org. Chem. 1978, 43, 286). This pair of enantiomers is herein after referred to as "trans compound".

Both the cis compound and trans compound, as well as mixtures thereof are effective as fungicides.

The tetrahydroisoquinoline derivative of the formula [IV] may preferably be produced by treating the tetrahydroisoquinoline derivative of the formula [III] in the presence of a solvent and a base at 60° C. to 250° C., preferably 100° C. to 200° C. for 5 minutes to 200 hours, preferably 30 minutes to 60 hours.

Preferred examples of the base employed in this reaction include carbonates and hydrogen carbonates of alkaline metals such as sodium carbonate, potassium carbonate, sodium hydrogen carbonate and potassium hydrogen carbonate. The amount of the base may usually be 0.1 to 10 equivalents per one equivalent of the tetrahydroisoquinoline of the formula [III].

Preferred examples of the solvent employed in this reaction include aromatic hydrocarbons such as toluene and xylene; ethers such as dioxane; polar solvents such as N,N-dimethylformamide (DMF), dimethylsulfoxide (DMSO), 1,3-dimethyl-2-imidazolidinone and hexamethyl phosphoric triamide (HMPA).

The tetrahydroisoquinoline derivative of the formula [III] employed as a starting material of this reaction may be cis compound, trans compound or mixtures thereof.

The tetrahydroisoquinoline derivatives of the present invention have strong fungicidal activities against wide variety of fungi causing diseases in plants. More particularly, the tetrahydroisoquinoline derivatives of the present invention have fungicidal activities against, for example, rice blast (*Pyricularia oryzae*), rice sheath blight (*Rhizoctonia solani*), rice brown spot (*Cochliobolus miyabeanus*), apple powdery mildew (*Podosphaera leucotricha*), apple scab (*Venturia inaegualis*), pear scab (*Venturia nashicola*), apple blossom blight (*Sclerotinia mali*), persimmon anthracnose (*Gloeosporium kaki*), peach brown rot (*Sclerotinia cinerea*), peach scab (*Cladosporium carpophilum*), Grape gray mold (*Botrytis cinerea*), grape anthracnose (*Elsinoe ampelina*), grape ripe rot (*Glomerella cingulata*), sugar beet cercospora leaf spot (*Cercospora beticola*), peanut brown leaf spot (*Cercospora arachidicola*), peanut leaf spot (*Cercospridium personatum*), barley powdery mildew (*Erysiphe graminis* f.sp. *hordei*), barley snow mold (*Fusarium nivale*), wheat powdery mildew (*Erysiphe graminis* f.sp. *tritici*), wheat leaf rust (*Puccinia recondita*), wheat eyespot (*Pseudocercosporella herpotrichoides*), wheat spot blotch (*Drechslera sorokiniana*), cucumber downy mildew (*Pseudoperonospora cubensis*), cucumber powdery mildew (*Sphaerotheca fuliginea*), cucumber gummy stem blight (*Mycosphaerella melonis*), cucumber gray mold (*Botrytis cinerea*), cucumber scab (*Cladosporium cucumerinum*), tomato late blight (*Phytophthora infestans*), tomato leaf mold (*Cladosporium fulvum*), tomato gray mold (*Botrytis cinerea*), strawberry powdery mildew (*Sphaerotheca humuli*), hop gray mold (*Botrytis cinerea*), tobacco powdery mildew (*Erysiphe cichoracearum*), rose black spot (*Diplocarpon rosae*), orange scab (*Elsinoe fawcetii*), orange blue mold (*Penicillium italicum*), orange common green mold (*Penicillium digitatum*) and the like. Among these, the compounds of the present invention exhibit especially strong fungicidal activities against wheat powdery mildew (*Erysiphe graminis* f.sp. *tritici*), wheat leaf rust (*Puccinia recondita*), wheat spot blotch (*Drechslera sorokiniana*), rice blast (*Pyricularia oryzae*)

and cucumber powdery mildew (*Sphaerotheca fuliginea*). The compounds of the present invention do not substantially damage the crops such as rice, wheat and cucumber, so that they are highly safe.

The fungicide according to the present invention, which contains the above-described tetrahydroisoquinoline derivative of the present invention may contain the tetrahydroisoquinoline derivative alone, but usually contains an agriculturally acceptable carrier, surfactant, dispersing agent and/or other additives and is formulated into, for example, wettable powder, emulsifiable concentrate, powder or granules. These formulations may be applied directly or after diluting to an appropriate concentration. The content of the tetrahydroisoquinoline derivative in the fungicide composition may be appropriately selected and may preferably be 0.5-80% by weight with respect to the overall composition.

The amount of the fungicide to be applied to the plants differs depending on the tetrahydroisoquinoline derivative contained therein, the disease to be treated, the degree of the disease, environment and on the formulation form of the fungicide. In cases where the formulation form of the fungicide is one which is directly applied, such as powder or granules, the amount of the fungicide to be applied may preferably be 1-5000 g, more preferably 5-1000 g per 10 ares in terms of the amount of the active ingredient. In cases where the fungicide is finally used in the form of liquid, such as emulsifiable concentrate or wettable powder, the concentration of the active ingredient in the liquid to be applied may preferably be 0.1-10,000 ppm, more preferably 1-3000 ppm.

The present invention will now be described by way of examples thereof. It should be noted that the examples are presented for the illustration purpose only and should not be interpreted in any restrictive way.

EXAMPLE 1

Production of 3-(4-t-butylphenyl)-2-methyl-1,2,3,4-tetrahydroisoquinoline (Compound No. 5)

To 20 ml of THF in which 0.83 g of lithium aluminum hydride is suspended, 20 ml of a solution containing 0.32 g of 3-(4-t-butylphenyl)-2-methyl-1-oxo-1,2,3,4-tetrahydroisoquinoline in THF was added and the mixture was heated to reflux for 4 hours. After the reaction, 10 ml of 10% aqueous sodium hydroxide solution was gradually added to the resulting mixture cooled in iced water and the generated precipitates were removed by filtration through Celite. After concentrating the filtrate, the aqueous layer was extracted with ethyl acetate (40 ml×2). After washing the combined organic layers with brine (50 ml×1), the organic layers were dried over anhydrous magnesium sulfate. After evaporating the solvent under reduced pressure, the residue was purified by silica gel column chromatography [hexane/ethyl acetate (6/1)] to obtain 0.24 g of 3-(4-t-butylphenyl)-2-methyl-1,2,3,4-tetrahydroisoquinoline.

m.p.: 53°-54.5° C.

$^1$H-NMR (CDCl$_3$, δ ppm)
1.30(s,9H), 2.13(s,3H), 2.88-4.22(m,5H), 7.06(s,4H), 7.27(s,4H)

IR (NaCl, cm$^{-1}$)
2970, 2770, 1510, 1455, 1370, 840, 740

Elementary Analysis(%): as C$_{20}$H$_{25}$N
Found: C;86.26, H;9.17, N;4.61
Calcd.: C;85.97, H;9.01, N;5.01

The tetrahydroisoquinoline derivatives represented by the formula [I] according to the present invention which were obtained in essentially the same manner as in Example 1, as well as their properties are summarized in Table 1.

EXAMPLE 2

Production of 3-(4-hydroxyphenyl)-2-methyl-1,2,3,4-tetrahydroisoquinoline (Compound No. 44)

To 30 ml of 3-(4-methoxyphenyl)-2-methyl-1,2,3,4-tetrahydroisoquinoline (Compound No. 19) in benzene, 0.85 g of aluminum chloride was added and the resulting mixture was heated to reflux for 5 hours. After completion of the reaction, the reaction mixture was allowed to cool and water was added thereto. The generated precipitates were removed by filtration through Celite. The filtrate was made alkaline with saturated aqueous sodium hydrogen carbonate solution, and the resultant was extracted with ethyl acetate. After drying the combined organic layers over anhydrous magnesium sulfate, the solvent was evaporated under reduced pressure. The residue was purified by silica gel column chromatography [hexane/ethyl acetate (1/1)] to obtain 0.28 g of 3-(4-hydroxyphenyl)-2-methyl-1,2,3,4-tetrahydroisoquinoline.

m.p.: decomposed at 193° C.

1H-NMR (CDCl$_3$+DMSO-d6, δ ppm)
2.09(s,3H), 2.80-4.18(m,5H), 6.74(d,J=8Hz,2H), 6.90-7.27(m,6H), 8.83(bs,1H)

IR (KBr, cm$^{-1}$)
3440, 2960, 2800, 1615, 1590, 1520, 1470, 1280, 1260, 1240, 840, 750

Elementary Analysis(%): as C$_{16}$H$_{17}$NO
Found: C;79.92, H;7.27, N;5.75
Calcd.: C;80.30, H;7.15, N;5.85

EXAMPLE 3

Production of 3-(4-t-butylphenyl)-2-methyl-1,2,3,4-tetrahydroisoquinoline hydrogen chloride salt (Compound No. 45)

In 50 ml of a solution containing 0.75 g of 3-(4-t-butylphenyl)-2-methyl-1,2,3,4-tetrahydroisoquinoline in ether, hydrogen chloride gas was bubbled for 40 minutes at room temperature under stirring. The generated crystals were collected by filtration and washed with ether to obtain 0.7 g of 3-(4-t-butylphenyl)-2-methyl-1,2,3,4-tetrahydroisoquinoline hydrogen chloride salt m.p.: decomposed at 243° C.

IR (KBr, cm$^{-1}$)
2960, 2450, 1460, 840, 750, 580

Examples of formulations of the fungicides of the present invention will now be described. It should be noted that any of the tetrahydroisoquinoline derivatives according to the present invention may be formulated in essentially the same manner as in the examples which follow. In the formulation examples, all parts are by weight.

Formulation Example 1 (Wettable Powder)

Ten parts of the Compound No. 1 according to the present invention was mixed with 87.3 parts of Zeaklite (trade name, commercially available from Kunimine Kogyo) as a carrier, 1.35 parts of Neopelex (a surfactant commercially available from Kao Atlas Corporation) and 1.35 parts of Solpol 800A (a surfactant commercially available from Toho Kagaku Kogyo) and the mixture was pulverized to obtain 10% wettable powder.

Formulation Example 2 (Emulsifiable Concentrate)

Five parts of the Compound No. 2 of the present invention was mixed with 85 parts of xylene and 10 parts of Solpol 800A as a surfactant to obtain 5% emulsifiable concentrate.

Formulation Example 3 (Powder)

Two parts of the Compound No. 3 of the present invention was uniformly mixed with 5 parts of diatomaceous earth and 93 parts of clay and the mixture was pulverized to obtain 2% powder.

Formulation Example 4 (Granules)

Ten parts of the Compound No. 4 of the present invention was mixed with 50 parts of bentonite, 35 parts of Kunilite (trade name, commercially available from Kunimine Kogyo) and 5 parts of Solpol 800A as a surfactant and the mixture was pulverized. Ten parts of water was added to the mixture and the resultant was uniformly stirred. The resultant was extruded through sieve holes with a diameter of 0.7 mm and dried. The resultant was cut into the length of 1-2 mm to obtain 10% granules.

EXAMPLE 4

Effectiveness for Protection Against Wheat Powdery Mildew

In a plastic pot sizing 8 cm×8 cm, seeds of wheat (variety: Norin No. 61) were sown and the plants were grown in a green house. To the seedlings of wheat in which the primary leaf was completely expanded, a liquid formulated by diluting the wettable powder prepared as in Formulation Example 1 to a prescribed concentration shown in Table 2 below was applied. After drying the plants in the air, seedlings were inoculated with spores of wheat powdery mildew and were incubated in growth chamber at 25° C. Seven days after the inoculation, the degree of damage of the overall pot was examined and the prevention value was calculated therefrom. The degree of damage is defined as follows:

$$\text{Degree of Damage (\%)} = \frac{(n1 \times 1) + (n2 \times 2) + (n3 \times 3) + (n4 \times 4)}{4N} \times 100$$

N: total number of leaves examined
n0: number of leaves not diseased
n1: number of leaves in which the area of diseased spots is less than 25% and more than 0%
n2: number of leaves in which the area of diseased spots is 25-50%
n3: number of leaves in which the area of diseased spots is 50-75%
n4: number of leaves in which the area of diseased spots is more than 75%

The prevention value (%) is defined as follows:

$$\text{Prevention Value (\%)} = \left(1 - \frac{\text{Degree of Damage in Treated Group}}{\text{Degree of Damage in Non-Treated Group}}\right) \times 100$$

The effectiveness for preventing the disease was rated into 6 ranks as follows:

Rank 5: The prevention value is 90% or more
Rank 4: The prevention value is not less than 80% and less than 90%
Rank 3: The prevention value is not less than 70% and less than 80%
Rank 2: The prevention value is not less than 60% and less than 70%
Rank 1: The prevention value is not less than 50% and less than 60%
Rank 0: The prevention value is less than 50%
The results are shown in Table 2.

EXAMPLE 5

Effectiveness for Curing Wheat Powdery Mildew

In a plastic pot sizing 8 cm×8 cm, seeds of wheat (variety: Norin No. 61) were sown and the plants were grown in a green house. To the seedlings of wheat in which the primary leaf was completely expanded, spores of wheat powdery mildew was inoculated, and the plants was grown in an incubator at 25° C. On Day 1, Day 2, Day 3 and Day 4 after the inoculation, a liquid formulated by diluting the wettable powder prepared as in Formulation Example 1 to a concentration of the active ingredient of 250 ppm was applied and the plants were again incubated in growth chamber. Seven days after the inoculation, the degree of damage of the overall pot was examined and the prevention value was calculated therefrom in the same manner as in Example 4. The effectiveness for curing the disease was also rated into 6 ranks as in Example 4.

As a result, as for the Compound No. 5, the effectiveness for curing the disease was Rank 5 for the treatments on Day 1, Day 2, Day 3 and Day 4.

EXAMPLE 6

Effectiveness for Protection Against Wheat Leaf Rust

In a plastic pot sizing 8 cm×8 cm, seeds of wheat (variety: Norin No. 61) were sown and the plants were grown in a green house. To the seedlings of wheat in which the primary leaf was completely expanded, a liquid formulated by diluting the wettable powder prepared as in Formulation Example 1 to a prescribed concentration shown in Table 3 below was applied. After drying the plants in the air, seedlings were inoculated with spores of wheat leaf rust and were incubated in growth chamber at 25° C. Seven days after the inoculation, the degree of damage of the overall pot was examined and the prevention value was calculated therefrom in the same manner as in Example 4. The effectiveness for preventing the disease was also rated into 6 ranks as in Example 4.

The results are shown in Table 3.

EXAMPLE 7

Effectiveness for Protection Against Rice Blast

In a plastic pot sizing 8 cm×8 cm, seeds of rice (variety: Yamahoshi) were sown and the plants were grown in a green house. When the plants were grown to have 2.5-3 leaves, a liquid prepared by diluting the wettable powder prepared as in Formulation Example 1 to a concentration of the active ingredient of 500 ppm was applied. After drying in the air, seedlings were inoculated with spores of rice blast and were incubated in growth chamber at 25° C. Seven days after the inoculation, the degree of damage of the overall pot was examined and the prevention value was calculated therefrom as in Example 4. The effectiveness for preventing the disease was also rated into 6 ranks as in Example 4.

As for the Compound Nos. 21 and 44, the effectiveness for preventing the disease was Rank 5 and Rank 4, respectively.

EXAMPLE 8

Effectiveness for Protection Against Wheat Spot Blotch

In a plastic pot sizing 8 cm×8 cm, seeds of wheat (variety: Norin No. 61) were sown and the plants were grown in a green house. To the seedlings of wheat in which the primary leaf was completely expanded, a liquid formulated by diluting the wettable powder prepared as in Formulation Example 1 to a prescribed concentration shown in Table 4 below was applied. After drying the plants in the air, seedlings were inoculated with spores of wheat spot blotch and were incubated in growth chamber at 25° C. Seven days after the inoculation, the degree of damage of the overall pot was examined and the prevention value was calculated therefrom as in Example 4. The effectiveness for preventing the disease was also rated into 6 ranks as in Example 4.

The results are shown in Table 4.

EXAMPLE 9

Effectiveness for Protection Against Cucumber Powdery Mildew

In a plastic pot sizing 8 cm×8 cm, seeds of cucumber (variety: seiho) were sown and the plants were grown in a green house. To the seedlings of cucumber in which the primary true leaf was completely expanded, a liquid formulated by diluting the wettable powder prepared as in Formulation Example 1 to a concentration of the active ingredient of 500 ppm was applied. After drying the plants in the air, seedlings were inoculated with spores of cucumber powdery mildew and were incubated in growth chamber at 25° C. Ten days after the inoculation, the degree of damage of the overall pot was examined and the prevention value was calculated therefrom as in Example 4. The effectiveness for preventing the disease was also rated into 6 ranks as in Example 4.

As a result, as for the Compound No. 7, the effectiveness for preventing the disease was Rank 5.

EXAMPLE 10

Production of 3-(4-t-butylphenyl)-4-hydroxycarbonyl-2-methyl-1-oxo-1,2,3,4-tetrahydroisoquinoline (Compound Nos. 46 and 47)

To 170 ml of a solution containing 18.67 g of N-(4-t-butylbenzylidene)methylamine in acetonitrile, 18.00 g of homophthalic anhydride was added and the mixture was allowed to react at room temperature for 14 hours. After evaporating the solvent under reduced pressure, the residue was purified by silica gel column chromatography [chloroform/ethyl acetate (6/1)] to obtain 33.73 g of 3-(4-t-butylphenyl)-4-hydroxycarbonyl-2-methyl-1-oxo-1,2,3,4-tetrahydroisoquinoline (mixture of diastereomers). The thus obtained mixture of diastereomers was again subjected to silica gel column chromatography [chloroform/ethyl acetate (6/1)] to obtain 15.2 g of cis compound and 8.03 g of trans compound.

Compound No. 46 (cis compound)

$^1$H-NMR (DMSO-d6, δ ppm)
  1.28(s,9H), 2.98(s,3H), 4.82(d,J=6Hz,1H), 5.17(d,J=6Hz,1H), 6.92-7.09(m,5H), 8.02-8.17(m,1H)

IR (KBr, cm$^{-1}$)
  3080, 2960, 1745, 1630, 1180

Elementary Analysis (%): as $C_{21}H_{23}NO_3$
  Found: C;74.88, H;6.95, N;4.42
  Calcd.: C;74.75, H;6.87, N;4.15

Compound No. 47 (trans compound)
m.p.: decomposed at 252° C.

$^1$H-NMR (DMSO-d6, δ ppm)
  1.28(s,9H), 3.06(s,3H), 4.20(s,1H), 5.35(s,1H), 7.00-7.58(m,5H), 7.92-8.07(m, 1H)

IR (KBr, cm$^{-1}$)
  2950, 1740, 1620, 1475, 1400, 1265, 700

Elementary Analysis (%): as $C_{21}H_{23}NO_3$
  Found: C;74.69, H;6.75, N;4.43
  Calcd.: C;74.75, H;6.87, N;4.15

The tetrahydroisoquinoline derivatives represented by the formula [III] according to the present invention which were obtained in essentially the same manner as in Example 10, as well as their properties are summarized in Table 5.

EXAMPLE 11

Production of 3-(4-t-butylphenyl)-2-methyl-1-oxo-1,2,3,4-tetrahydroisoquinoline (Compound No. 85)

To 50 ml of a solution containing 9.00 g of 3-(4-t-butylphenyl)-4-hydroxycarbonyl-2-methyl-1-oxo-1,2,3,4-tetrahydroisoquinoline in dimethylsulfoxide, 4.20 g of sodium carbonate was added and the mixture was allowed to react at 150° C. for 1 hour. After the reaction, the solvent was evaporated under reduced pressure, and 800 ml of water was added thereto, followed by extraction with ethyl acetate (100 ml×5). The combined organic layers were washed with water (300 ml×6) and then with brine, and were dried over anhydrous magnesium sulfate. After evaporating the solvent under reduced pressure, the residue was purified by silica gel column chromatography [hexane/ethyl acetate (2/1)] to obtain 5.92 g of 3-(4-t-butylphenyl)-2-methyl-1-oxo-1,2,3,4-tetrahydroisoquinoline.

m.p.: 116°-117° C.

$^1$H-NMR (CDCl$_3$—d$_6$, δ ppm)
  1.20(s,9H), 2.74-3.20(m,4H), 3.61(dd,J=7 Hz,16 Hz,1H), 4.69(dd,J=3 Hz,7 Hz,1H), 6.70-7.38(m,7H), 7.82-8.16(m,1H)

IR (KBr, cm$^{-1}$)
  2950, 1650, 1605, 1475, 1400, 1265, 825, 740

Elementary Analysis (%): as $C_{20}H_{23}NO$
  Found: C;81.63, H;7.73, N;4.76
  Calcd.: C;81.87, H;7.90, N;4.77

The tetrahydroisoquinoline derivatives represented by the formula [IV] according to the present invention which were obtained in essentially the same manner as in Example 11, as well as their properties are summarized in Table 6.

EXAMPLE 12

Production of 3-(4-hydroxyphenyl)-2-methyl-1-oxo-1,2,3,4-tetrahydroisoquinoline (Compound No. 125)

To 500 ml of a solution containing 10 g of 3-(4-methoxyphenyl)-2-methyl-1-oxo-1,2,3,4-tetrahydroisoquinoline in benzene, 20 g of aluminum chloride was added and the mixture was heated to reflux for 7 hours. After allowing the resulting mixture to cool, water was added thereto and the generated insoluble materials were removed by filtration through Celite. The filtrate was extracted with ethyl acetate and the combined organic layers were washed with brine, followed by drying over anhydrous magnesium sulfate. After evaporating the solvent, the residue was purified by silica gel column chromatography [hexane/ethyl acetate (2/1) to obtain 5.34 g of 3-(4-hydroxyphenyl)-2-methyl-1-oxo-1,2,3,4-tetrahydroisoquinoline.

m.p.: 182°–183.5° C.

$^1$H-NMR (CDCl3+DMSO-d$_6$, δ ppm)
2.72–4.00(m,5H), 4.66(dd,J=3 Hz,7 Hz,1H), 6.50–7.60(m,7H), 7.72–8.28(m, 1H), 8.82(s,1H)

IR (KBr, cm$^{-1}$)
3150, 1620, 1570, 1515, 1265, 725

Elementary Analysis (%): as C$_{16}$H$_{15}$NO$_2$
Found: C;76.07, H;5.80, N;5.56
Calcd.: C;75.86, H;5.96, N;5.52

EXAMPLE 13

Production of 3-(4-isopropyloxyphenyl)-2-methyl-1-oxo- 1,2,3,4-tetrahydroisoquinoline (Compound No. 126)

To 20 ml of a solution containing 1.50 g of 3-(4-hydroxyphenyl)-2-methyl-1-oxo-1,2,3,4-tetrahydroisoquinoline, 0.86 g of potassium carbonate and 1.24 ml of isopropyl iodide were added and the resulting mixture was heated to reflux for 21 hours. After allowing the mixture to cool, water was added thereto and the resultant was extracted with ethyl acetate. The combined organic layers were washed with brine and dried over anhydrous magnesium sulfate. After evaporating the solvent under reduced pressure, the residue was purified by silica gel column chromatography [hexane/ethyl acetate (2/1)] to obtain 1.53 g of 3-(4-isopropyloxyphenyl)-2-methyl-1-oxo-1,2,3,4-tetrahydroisoquinoline.

m.p.: 115°–116° C.

$^1$H-NMR (CDCl$_3$, δ ppm)
1.23(d,J=6 Hz,6H), 2.70–3.15(m,4H),
3.62(dd,J=7 Hz,16 Hz,1H), 4.20–4.80(m,2H), 6.52–7.45(m,7H), 7.90–8.27(m, 1H)

IR (KBr, cm$^{-1}$)
2980, 2900, 1640, 1510, 1240, 950, 835, 750

Elementary Analysis (%): as C$_{19}$H$_{21}$NO$_2$
Found: C;77.26; H;7.04, N;4.41
Calcd.: C;77.26, H;7.16, N;4.74

The tetrahydroisoquinoline derivatives represented by the formula [IV] according to the present invention which were obtained in essentially the same manner as in Example 13, as well as their properties are summarized in Table 7.

EXAMPLE 14

Effectiveness for Protection Against Wheat Powdery Mildew

The effectiveness of the tetrahydroisoquinoline derivatives represented by the formula [III] or [IV] against wheat powdery mildew (*Erysiphe graminis* f.sp. *tritici*) was tested in the same manner as in Example 4. The concentration of the active ingredient in the liquid applied to the plants was 500 ppm.

As a result, as for the Compound Nos. 48, 88, 115 and 120, the effectiveness for preventing the disease was Rank 5, and as for the Compound-Nos. 92, 97 and 100, the effectiveness was Rank 4.

EXAMPLE 15

Effectiveness for Protection Against Wheat Leaf Rust

The effectiveness of the tetrahydroisoquinoline derivatives represented by the formula [III] or [IV] according to the present invention against wheat leaf rust (*Puccinia recondita*) was tested in the same manner as in Example 6. The concentration of the active ingredient in the liquid applied to the plants was 500 ppm.

As a result, as for the Compound Nos. 100 and 104, the effectiveness was Rank 5, and as for the Compound Nos. 78, 83, 103, 115 and 129, the effectiveness was Rank 4.

EXAMPLE 16

Effectiveness for Protection Against Rice Blast

The effectiveness of the compounds represented by the formula [III] or [IV] against rice blast (*Pyricularia oryzae*) was tested in the same manner as in Example 7 (the concentration of the active ingredient in the liquid applied to the plants was 500 ppm).

As a result, as for the Compound No. 103, the effectiveness was Rank 5, and as for the Compound Nos. 55, 94 and 108, the effectiveness was Rank 4.

TABLE 1

| Compound No. | (structure with R$^2$, R$^3$, R$^4$, R$^5$, R$^6$) | R1 | Physical Properties | IR (cm−1) |
| --- | --- | --- | --- | --- |
| 1 | –⟨phenyl⟩–Me | Me | n$_D^{25.1}$ = 1.5835 | 2920, 2780, 1518 1458, 1370, 825 740 (NaCl) |
| 2 | –⟨phenyl⟩–\ | Me | n$_D^{25.0}$ = 1.5781 | 2970, 2780, 1455 1375, 840, 740 (NaCl) |

TABLE 1-continued

| # | Ar | R | Physical data | IR (cm⁻¹) |
|---|---|---|---|---|
| 3 | 4-isopropylphenyl | Me | $n_D^{25.2} = 1.5710$ | 2960, 2770, 1460, 1370, 840, 740 (NaCl) |
| 4 | 4-n-propylphenyl | Me | $n_D^{25.1} = 1.5707$ | 2960, 2930, 2770, 1460, 1370, 975, 740 (NaCl) |
| 6 | 4-n-butylphenyl | Me | $n_D^{25.2} = 1.5649$ | 2920, 1455, 1370, 965, 830, 740 (NaCl) |
| 7 | 4-sec-butylphenyl | Me | $n_D^{25.3} = 1.5601$ | 2960, 2760, 1455, 1370, 970, 840, 740 (NaCl) |
| 8 | 4-n-hexylphenyl | Me | $n_D^{25.4} = 1.5529$ | 2920, 1455, 1370, 1125, 970, 740 (NaCl) |
| 9 | 4-(N,N-dimethylamino)phenyl | Me | m.p. 89–91° C. | 2770, 1615, 1520, 1350, 820, 740 (KBr) |
| 10 | 4-chlorophenyl | Me | m.p. 68–73° C. | 2950, 2780, 1485, 1455, 1370, 1130 (KBr) |
| 11 | 4-bromophenyl | Me | m.p. 67–68° C. | 2955, 2780, 1495, 1455, 1130, 745, 705 (KBr) |
| 12 | 4-(trifluoromethyl)phenyl | Me | m.p. 67–68° C. | 2780, 1620, 1325, 1165, 1110, 1070, 840, 740 (KBr) |
| 13 | 4-biphenylyl | Me | m.p. 121–123° C. | 2775, 1485, 740 (KBr) |
| 14 | 3-methylphenyl | Me | $n_D^{25.0} = 1.5817$ | 2770, 1655, 1500, 1460, 1370, 740 (NaCl) |
| 15 | 3-methoxyphenyl | Me | $n_D^{25.1} = 1.5835$ | 2780, 1600, 1585, 1485, 1455, 1265, 740 (NaCl) |
| 16 | 3-bromophenyl | Me | m.p. 62–65° C. | 2780, 1495, 1455, 1375, 1130, 975, 745, 700 (NaCl) |

TABLE 1-continued
| 17 | 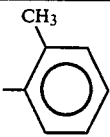 | Me | $n_D^{25.0} = 1.5863$ | 2770, 1495, 1455<br>1370, 970, 740<br>(NaCl) |
| --- | --- | --- | --- | --- |
| 18 | 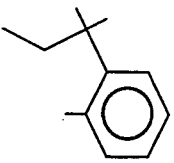 | Me | $n_D^{24.7} = 1.5591$ | 2960, 1460, 1370<br>970, 740<br>(NaCl) |
| 19 | 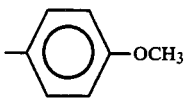 | Me | m.p. 44.5–46° C. | 2770, 1610, 1510<br>1240, 1035, 840<br>750 (KBr) |
| 20 | 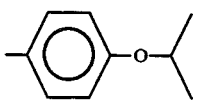 | Me | m.p. 89–90.5° C. | 2980, 2770, 1615<br>1510, 1240, 835<br>740 (KBr) |
| 21 | 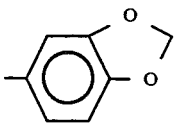 | Me | m.p. 84–85.5° C. | 2770, 1500, 1490<br>1440, 1250, 1235<br>1140, 750 (KBr) |
| 22 | 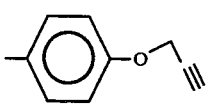 | Me | $n_D^{25.1} = 1.5973$ | 3300, 2920, 2770<br>2110, 1610, 1510<br>1210, 1030, 835<br>745 (NaCl) |
| 23 | 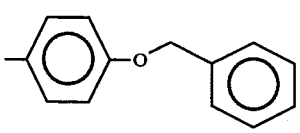 | Me | m.p. 108–110° C. | 2760, 1610, 1510<br>1240, 1115, 840<br>740 (KBr) |
| 24 | 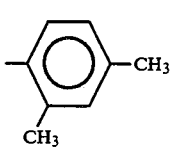 | Me | $n_D^{25.0} = 1.5819$ | 2920, 1500, 1455<br>1370, 740<br>(NaCl) |
| 25 | 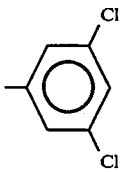 | Me | Viscose Oil | 3005, 1600, 1480<br>740 (NaCl) |
| 26 | 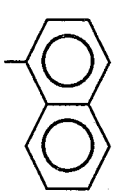 | Me | m.p. 90–92° C. | 2780, 1455, 1370<br>805, 780, 740<br>(KBr) |
| 27 | 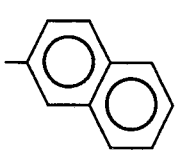 | Me | m.p. 94–96° C. | 2780, 1505, 1375<br>1130, 860, 835<br>745 (KBr) |

TABLE 1-continued

| # | Aryl | R | Phys. | IR |
|---|---|---|---|---|
| 28 | 2,4,6-tri(CH₃O)-phenyl (CH₃O at 2,4; CH₃O at 6) | Me | m.p. 140–141° C. | 2850, 2795, 1630, 1590, 1455, 1220, 1150, 1100, 820, 750 (KBr) |
| 29 | 2,3-di(CH₃O)-phenyl | Me | m.p. 63–64.5° C. | 2950, 1565, 1500, 1465, 1405, 1235, 1140, 740 (KBr) |
| 30 | phenyl | Et | $n_D^{25.0} = 1.5520$ | 2970, 1510, 1380, 1360, 1110, 840, 740 (NaCl) |
| 31 | phenyl | i-Pr | m.p. 80–82° C. | 2960, 1365, 1170, 840, 740 (KBr) |
| 32 | 3-CH₃O-phenyl | i-Pr | m.p. 62–63° C. | 2960, 1500, 1410, 1240, 1045, 740 (KBr) |
| 33 | phenyl | −CH₂−C≡CH | m.p. 71–73° C. | 3280, 2955, 1120, 835, 740 (KBr) |
| 34 | phenyl | −CH₂−CH=CH−CH₃ | $n_D^{25.1} = 1.5611$ | 2970, 1510, 1105, 920, 840, 740 (NaCl) |
| 35 | phenyl | t-Bu | $n_D^{25.1} = 1.5526$ | 2970, 1460, 1395, 1365, 1200, 835, 745 (NaCl) |
| 36 | phenyl | i-Pr | $n_D^{25.1} = 1.5615$ | 2970, 1460, 1385, 1360, 1170, 835, 740 (NaCl) |
| 37 | 4-i-Pr-phenyl | −CH₂−CH=CH−CH₃ | $n_D^{25.0} = 1.5693$ | 2960, 1510, 1460, 1420, 1105, 920, 840, 745 (KBr) |
| 38 | 4-i-Pr-phenyl | −CH₂−C≡CH | $n_D^{25.1} = 1.5735$ | 3300, 2970, 1430, 1105, 840, 745 (NaCl) |
| 39 | 4-OCH₃-phenyl | i-Pr | m.p. 68–69° C. | 2970, 1615, 1510, 1255, 1175, 1035, 835, 740 (KBr) |

TABLE 1-continued

| | | | | |
|---|---|---|---|---|
| 40 | -⟨○⟩-OCH₃ | ∼∕ | m.p. 64–66° C. | 2940, 2805, 1615 1515, 1255, 1035 840, 740 (KBr) |
| 41 | -⟨○⟩-OCH₃ | ∼≡ | $n_D^{24.9} = 1.5920$ | 3295, 2920, 1615 1515, 1250, 1040 840, 745 (NaCl) |
| 42 | -⟨○⟩-CH₃ | i-Pr | $n_D^{25.1} = 1.5716$ | 2970, 1510, 1175 820, 740 (NaCl) |
| 43 | -⟨○⟩-CF₃ | i-Pr | $n_D^{26.6} = 1.5288$ | 2970, 1620, 1325 1115, 1070, 740 (NaCl) |

| Compound No. | NMR (δ ppm) | Elementary Analysis (%) (calculated values) |
|---|---|---|
| 1 | 2.13(s, 3H), 2.32(s, 3H) 2.85–4.31(m, 5H), 7.17(s, 4H) (CDCl3) | as C17H19N C; 86.40, H; 7.99, N; 5.87 (C; 86.03, H; 8.06, N; 5.90) |
| 2 | 1.20(t, J=8Hz, 3H), 2.13(s, 3H), 2.61(q, J=8Hz, 2H), 2.85–4.20(m, 5H) 7.03(s, 4H), 7.19(s, 4H) (CDCl3) | as C18H21N C; 86.38, H; 8.36, N; 5.58 (C; 86.00, H; 8.42, N; 5.57) |
| 3 | 1.24(d, J=7Hz, 6H), 2.17(s, 3H) 2.88–4.23(m, 6H), 7.07(s, 4H) 7.21(s, 4H) (CDCl3) | as C19H23N C; 85.73, H; 8.73, N; 4.88 (C; 85.98, H; 8.73, N; 5.27) |
| 4 | 0.93(t, J=6Hz, 3H), 1.32–1.95(m, 2H) 2.17(s, 3H), 2.32–4.20(m, 7H) 6.85–7.33(m, 8H) (CDCl3) | as C19H23N C; 85.62, H; 8.68, N; 5.39 (C; 85.98, H; 8.73, N; 5.27) |
| 6 | 0.69–1.88(m.7H), 2.12(s, 3H) 2.30–4.21(m, 7H), 6.82–7.38(m, 8H) (CDCl3) | as C20H25N C; 85.78, H; 9.26, N; 4.85 (C; 85.97, H; 9.02, N; 5.01) |
| 7 | 0.71(t, J=7Hz, 3H), 1.31(s, 6H), 1.66(q, J=7Hz, 2H), 2.19(s, 3H) 3.00(dd, J=17Hz, 4Hz, 1H), 3.18(dd, J=17Hz, 10Hz, 1H) 3.41(dd, J=10Hz, 4Hz, 1H), 3.61(d, J=16Hz, 1H) 4.03(d, J=16Hz, 1H), 7.04–7.37(m, 8H) (CDCl3) | as C21H27N C; 86.24, H; 9.05, H; 4.94 (C; 85.95, H; 9.27, N; 4.77) |
| 8 | 0.66–1.95(m, 11H), 2.18(s, 3H) 2.36–4.21(m, 7H), 6.85–7.47(m, 8H) (CDCl3) | as C22H29N C; 85.66, H; 9.33, N; 4.34 (C; 85.94, H; 9.51, N; 4.56) |
| 9 | 2.13(s, 3H), 2.84–4.20(m, 11H) 6.68(d, J=8Hz, 2H), 6.92–7.32(m, 6H) (CDCl3) | as C18H22N2 C; 81.42, H; 8.46, N; 10.11 (C; 81.16, H; 8.32, N; 10.51) |
| 10 | 2.13(s, 3H), 2.84–4.20(m, 5H) 7.08(s, 4H), 7.26(s, 4H) (CDCl3) | as C16H16NCl C; 74.94, H; 6.24, N; 5.79 (C; 74.55, H; 6.25, N; 5.43) |
| 11 | 2.14(s, 3H), 2.87–4.24(m, 5H) 7.03(s, 4H), 7.28(s, 4H) (CDCl3) | as C16H16NBr C; 63.83, H; 5.24, N; 4.65 (C; 63.59, H; 5.33, N; 4.63) |
| 12 | 2.18(s, 3H), 2.88–4.27(m, 5H) 7.10(s, 4H), 7.31–7.78(s, 4H) (CDCl3) | as C17H16NF3 C; 70.12, H; 5.41, N; 4.63 (C; 70.09, H; 5.53, N; 4.80) |
| 13 | 2.20(s, 3H), 2.90–4.27(m, 5H) 6.90–7.67(m, 13H) (CDCl3) | as C22H21N C; 88.18, H; 6.89, N; 4.82 (C; 88.25, H; 6.89, N; 4.82) |
| 14 | 2.10(s, 3H), 2.30(S, 3H) 2.80–4.20(m, 5H), 6.72–7.30(m, 8H) (CDCl3) | as C17H19N C; 86.06, H; 7.89, N; 5.68 (C; 86.03, H; 8.07, N; 5.90) |
| 15 | 2.20(s, 3H), 2.62–4.23(m, 8H) 6.68–7.41(m, 8H) (CDCl3) | as C17H19NO C; 80.57, H; 7.38, N; 5.14 (C; 80.59, H; 7.55, N; 5.52) |
| 16 | 2.13(s, 3H), 2.83–4.20(m, 5H) 7.00(s, 4H), 7.24(s, 4H) (CDCl3) | as C16H16NBr C; 63.32, H; 5.24, N; 5.01 (C; 63.59, H; 5.33, N; 4.63) |
| 17 | 2.17(s, 3H), 2.40(s, 3H) 2.80–4.30(m, 5H), 6.90–7.63(m, 8H) (CDCl3) | as C17H19N C; 85.86, H; 7.89, N; 5.99 (C; 86.03, H; 8.07, N; 5.90) |
| 18 | 0.70(t, J=7Hz, 2H), 1.31(s, 6H), 1.63(q, J=7Hz, 2H), 2.19(s, 3H) 3.05(dd, J=17Hz, 5Hz, 1H), 3.18(dd, J=17Hz, 10Hz, 1H) 3.41(dd, J=10Hz, 5Hz, 1H), 3.62(d, J=16Hz, 1H) 4.03(d, J=16Hz, 1H), 7.06–7.21(m, 4H), 7.25–7.38(m, 3H) (CDCl3) | as C21H27N C; 85.96, H; 9.45, N; 4.97 (C; 85.95, H; 9.27, N; 4.77) |
| 19 | 2.11(s, 3H), 2.80–4.23(m, 8H) 6.60–7.43(m, 8H) (CDCl3) | as C17H19NO C; 80.55, H; 7.62, N; 5.56 (C; 80.59, H; 7.55, N; 5.52) |

TABLE 1-continued

| | | |
|---|---|---|
| 20 | 1.28(d, J=6Hz, 6H), 2.13(s, 3H), 2.86–4.23(m, 5H) 4.52(septet, J=6Hz, 1H) 6.70–7.34(m, 8H) (CDCl3) | as C19H23NO C; 81.47, H; 8.30, N; 5.24 (C; 81.09, H; 8.23, N; 4.97) |
| 21 | 2.17(s, 3H), 2.80–4.26(m, 5H) 5.94(s, 2H), 6.65–7.40(m, 7H) (CDCl3) | as C17H17NO2 C; 76.76, H; 6.35, N; 5.12 (C; 76.38, H; 6.40, N; 5.23) |
| 22 | 2.13(s, 3H), 2.49(t, J=2Hz, 1H) 1.70–4.23(m, 5H), 4.64(d, J=2Hz, 2H) 6.80–7.48(m, 8H) (CDCl3) | as C19H19NO C; 82.21, H; 6.83, N; 5.28 (C; 82.27, H; 6.90, N; 5.04) |
| 23 | 2.21(s, 9H), 2.92–3.27(m, 2H), 3.35–3.48(m, 1H) 3.62(d, J=15Hz, 1H), 4.03(d, J=15Hz, 1H), 5.12(s, 2H) 6.92–7.60(m, 13H) (CDCl3) | as C23H23NO C; 83.80, H; 7.30, N; 4.53 (C; 83.85, H; 7.04, N; 4.25) |
| 24 | 2.12(s, 3H), 2.27(s, 3H) 2.32(s, 3H), 2.75–4.25(m, 5H) 6.76–7.42(m, 7H) (CDCl3) | as C18H21N C; 86.04, H; 8.24, N; 5.35 (C; 86.01, H; 8.42, N; 5.57) |
| 25 | 2.09(s, 3H), 2.74–4.17(m, 5H) 6.88–7.48(m, 7H) (Acetone-d6) | as C16H15C12N C; 65.80, H; 4.99, N; 4.58 (C; 85.97, H; 9.02, N; 5.01) |
| 26 | 2.16(s, 3H), 2.68–4.33(m, 5H) 6.83–8.02(m, 10H), 8.37–8.80(m, 1H) (CDCl3) | as C20H19N C; 87.63, H; 6.81, N; 5.40 (C; 87.87, H; 7.00, N; 5.12) |
| 27 | 2.18(s, 3H), 2.78–4.30(m, 5H) 7.60(s, 4H), 7.23–8.00(m, 7H) (CDCl3) | as C20H19N C; 87.90, H; 7.14, N; 5.06 (C; 87.87, H; 7.00, N; 5.12) |
| 28 | 2.34(s, 3H), 2.80–4.33(m, 14H) 5.97–6.12(m, 2H), 7.04(s, 4H) (CDCl3) | as C19H23NO3 C; 72.62, H; 7.49, N; 4.58 (C; 72.81, H; 7.39, N; 4.46) |
| 29 | 1.33(s, 9H), 2.21(s, 3H), 2.90–3.18(m, 2H) 3.63(d, J=15Hz, 1H), 3.84(S, 3H), 4.02(d, J=15Hz, 1H) 6.85–7.38(m, 7H) (CDCl3) | as C21H27NO C; 81.54, H; 8.61, N; 4.31 (C; 81.51, H; 8.79, N; 4.53) |
| 30 | 1.04(t, J=6Hz, 3H), 1.30(s, 9H) 1.90–4.32(m, 7H), 7.08(s, 4H) 7.27(s, 4H) (CDCl3) | as C21H27N C; 85.62, H; 9.10, N; 4.75 (C; 85.95, H; 9.27, N; 4.77) |
| 31 | 0.60–1.46(m, 15H), 2.70–4.02(m, 6H) 7.00(s, 4H), 7.21(s, 4H) (CDCl3) | as C22H29N C; 85.99, H; 9.49, N; 4.72 (C; 85.93, H; 9.50, N; 4.55) |
| 32 | 0.88(d, J=9Hz, 3H), 1.13(d, J=9Hz, 3H), 1.32(s, 9H) 2.89–3.13(m, 3H), 3.75–4.02(m, 5H), 4.33–4.42(m, 1H) 6.84–7.39(m, 7H) (CDCl3) | as C23H31NO C; 81.88, H; 9.08, N; 3.93 (C; 81.85, H; 9.26, N; 4.15) |
| 33 | 1.32(s, 9H), 2.20(t, J=2Hz, 1H) 2.94–4.24(m, 7H), 7.10(s, 4H) 7.31(s, 4H) (CDCl3) | as C22H25N C; 87.20, H; 8.31, N; 4.23 (C; 87.08, H; 8.30, N; 4.61) |
| 34 | 1.30(s, 9H), 2.47–4.28(m, 7H) 4.90–6.27(m, 3H), 7.02(s, 4H) 7.24(s, 4H) (CDCl3) | as C22H27N C; 86.19, H; 8.77, N; 4.97 (C; 86.50, H; 8.90, N; 4.58) |
| 35 | 1.03(s, 9H), 1.23(s, 9H), 2.72(dd, J=8Hz, 4Hz, 1H) 3.17(dd, J=8Hz, 6Hz, 1H), 3.94(s, 2H), 4.40(dd, J=6Hz, 4Hz, 1H) 6.86–7.28(m, 8H) (CDCl3) | as C23H31N C; 86.05, H; 9.59, N; 3.97 (C; 85.92, H; 9.71, N; 4.35) |
| 36 | 0.77–1.42(m, 12H), 2.56–3.36(m, 4H) 3.52–4.15(m, 3H), 6.84–7.40(m, 8H) (CDCl3) | as C21H27N C; 85.84, H; 9.20, N; 5.14 (C; 85.95, H; 9.27, N; 4.77) |
| 37 | 1.20(d, J=7Hz, 6H), 2.42–4.20(m, 8H) 4.86–5.34(m, 2H), 5.50–6.20(m, 1H) 6.86–7.38(m, 8H) (CDCl3) | as C21H25N C; 86.25, H; 8.67, N; 5.18 (C; 86.54, H; 8.64, N; 4.80) |
| 38 | 1.22(d, J=7Hz, 6H), 2.18(t, J=2Hz, 1H) 2.68–4.33(m, 8H), 6.93–7.40(m, 8H) (CDCl3) | as C21H23N C; 87.38, H; 7.97, N; 4.93 (C; 87.15, H; 8.00, N; 4.83) |
| 39 | 0.87(d, J=7Hz, 3H), 1.10(d, J=7Hz, 3H) 2.70–3.28(m, 3H), 3.53–3.98(m, 6H) 6.63–7.40(m, 8H) (CDCl3) | as C19H23NO C; 80.71, H; 8.28, N; 4.84 (C; 81.09, H; 8.23, N; 4.97) |
| 40 | 0.84(d, J=7Hz, 3H), 1.10(d, J=7Hz, 3H) 2.32(s, 3H), 2.67–3.42(m, 3H) 3.57–4.26(m, 3H), 6.77–7.52(m, 8H) (CDCl3) | as C19H21NO C; 81.65, H; 7.53, N; 4.71 (C; 81.68, H; 7.57, N; 5.01) |
| 41 | 2.17(t, J=2Hz, 1H), 2.82–4.30(m, 10H) 6.82(d, J=8Hz, 2H), 7.03(s, 4H) 7.26(d, J=8Hz, 2H) (CDCl3) | as C19H19NO C; 82.61, H; 7.06, N; 4.73 (C; 82.27, H; 6.90, N; 5.04) |
| 42 | 0.85(d, J=7Hz, 3H), 1.10(d, J=7Hz, 3H) 2.31(s, 3H), 2.65–3.42(m, 3H), 3.57–4.05(m, 3H) 6.77–7.52(m, 8H) (CDCl3) | as C19H23N C; 85.89, H; 8.73, N; 5.34 (C; 85.98, H; 8.73, N; 5.27) |
| 43 | 0.88(d, J=9Hz, 3H), 1.15(d, J=9Hz, 3H) 2.88–3.08(m, 3H), 3.75–4.02(m, 3H) 6.89–7.80(m, 8H) (CDCl3) | as C19H20F3N C; 71.40, H; 6.58, N; 4.67 (C; 71.46, H; 6.31, N; 4.39) |

TABLE 2

| Compound No. | Concentration of Effective Ingredient (ppm) | Rank of Effectiveness |
|---|---|---|
| 2 | 500 | 5 |
| 3 | 500 | 5 |
| 4 | 500 | 5 |
| 5 | 500 | 5 |
| | 50 | 5 |
| 6 | 500 | 5 |

TABLE 2-continued

| Compound No. | Concentration of Effective Ingredient (ppm) | Rank of Effectiveness |
| --- | --- | --- |
| 7 | 500 | 5 |
|  | 50 | 5 |
| 19 | 500 | 5 |
| 20 | 500 | 4 |
| 22 | 500 | 4 |
| 23 | 500 | 5 |
| 29 | 500 | 5 |
| 30 | 500 | 5 |
| 31 | 500 | 5 |
|  | 100 | 5 |
| 32 | 500 | 5 |
| 35 | 500 | 4 |
| 36 | 500 | 5 |
| 37 | 500 | 5 |
| 42 | 500 | 5 |
| 43 | 500 | 4 |
| 45 | 500 | 5 |

TABLE 3

| Compound No. | Concentration of Effective Ingredient (ppm) | Rank of Effectiveness |
| --- | --- | --- |
| 2 | 500 | 4 |
| 3 | 500 | 5 |
| 4 | 500 | 5 |
| 5 | 500 | 5 |
|  | 250 | 5 |
| 6 | 500 | 5 |

TABLE 3-continued

| Compound No. | Concentration of Effective Ingredient (ppm) | Rank of Effectiveness |
| --- | --- | --- |
| 7 | 500 | 5 |
|  | 50 | 5 |
| 8 | 500 | 5 |
| 9 | 500 | 4 |
| 10 | 500 | 4 |
| 14 | 500 | 5 |
| 19 | 500 | 4 |
| 20 | 500 | 5 |
| 21 | 500 | 4 |
| 22 | 500 | 5 |
| 24 | 500 | 5 |
| 29 | 500 | 4 |
| 30 | 500 | 5 |
| 31 | 500 | 4 |
| 32 | 500 | 5 |
| 35 | 500 | 5 |
| 36 | 500 | 5 |
| 45 | 500 | 5 |

TABLE 4

| Compound No. | Concentration of Effective Ingredient (ppm) | Rank of Effectiveness |
| --- | --- | --- |
| 2 | 500 | 4 |
| 3 | 500 | 5 |
| 19 | 500 | 4 |
| 30 | 500 | 5 |
| 45 | 500 | 4 |

TABLE 5

(Structure: benzene ring with substituents $R^8$, $R^9$, $R^{10}$, $R^{11}$, $R^{12}$)

| Compound No. | (aryl group) | R7 | Configuration | Physical Properties | IR (KBr, cm−1) |
| --- | --- | --- | --- | --- | --- |
| 48 | –C6H4–CH3 | Me | cis | decomposed at 189° C. | 3020, 1740, 1630, 1170 |
| 49 | –C6H4–CH3 | Me | trans | decomposed at 203° C. | 2920, 1735, 1715, 1640, 1260, 1165, 710 |
| 50 | –C6H4–CH2CH3 | Me | cis | decomposed at 207° C. | 3030, 1750, 1640, 1600, 1175, 700 |
| 51 | –C6H4–CH2CH3 | Me | trans | m.p. 130–131° C. | 2960, 1745, 1625, 1580, 1165, 700 |
| 52 | –C6H4–CH(CH3)2 | Me | cis | decomposed at 215° C. | 3040, 2950, 1740, 1630, 1175 |
| 53 | –C6H4–CH(CH3)2 | Me | trans | m.p. 163–164° C. | 2950, 1740, 1625, 1580, 1400, 1265, 1170, 705 |

TABLE 5-continued
| | | | | | |
|---|---|---|---|---|---|
| 54 | 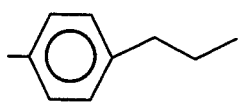 | Me | cis | m.p. 190–192° C. | 3030, 2950, 1745 1630, 1175, 750 680 |
| 55 | 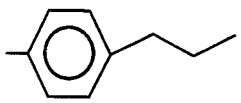 | Me | trans | m. p. 139–140° C. | 1230, 700 |
| 56 | 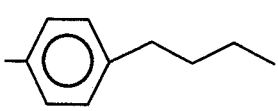 | Me | trans | m.p. 137–138° C. | 2920, 1740, 1620 1475, 1400, 1265 1165, 700 |
| 57 | 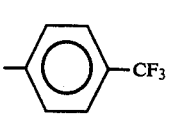 | Me | cis | decomposed at 203° C. | 3050, 1750, 1640 1330, 1175, 1125 |
| 58 | 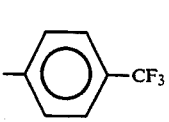 | Me | trans | m.p. 103–105° C. | 2930, 1720, 1640 1325, 1170, 1120 1070, 1020, 705 |
| 59 | 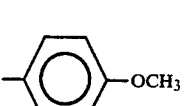 | Me | cis | decomposed at 178° C. | 3080, 1745, 1630 1505, 1250, 1170 835 |
| 60 | 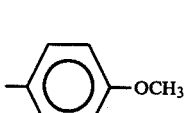 | Me | trans | decomposed at 155° C. | 2930, 1700, 1645 1510, 1250, 1180 1040, 840 |
| 61 |  | Me | cis | decomposed at 208° C. | 3050, 1745, 1635 1490, 1400, 1175 840, 735 |
| 62 |  | Me | trans | m.p. 146–147° C. | 1575, 1495, 1400 1265, 1600, 710 |
| 63 | 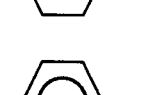 | Me | cis | decomposed at 209° C. | 3050, 1740, 1635 1480, 1400, 1175 |
| 64 |  | Me | trans | decomposed at 214° C. | 3020, 2900, 1710 1640, 1490, 1400 1265, 830, 740 |
| 65 | 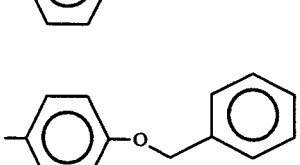 | Me | trans | decomposed at 215° C. | 2900, 1725, 1630 1510, 1240, 1180 700 |
| 66 | 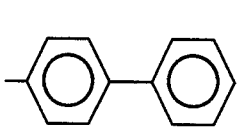 | Me | cis | decomposed at 210° C. | 3020, 1745, 1620 1165, 700 |

TABLE 5-continued
| | | | | | |
|---|---|---|---|---|---|
| 67 | 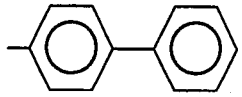 | Me | trans | decomposed at 185° C. | 3480, 2910, 1720 1625, 1600, 1480 1260, 700 |
| 68 | 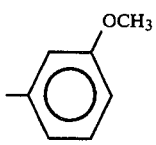 | Me | cis | decomposed at 190° C. | 2950, 1750, 1620 1600, 1565, 1290 1260, 1180, 700 |
| 69 | 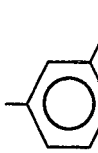 | Me | cis | m.p. 194–195° C. | 1570, 1180, 700 |
| 70 | 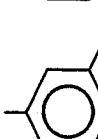 | Me | trans | decomposed at 177° C. | 2920, 1745, 1700 1660, 1620, 1265 1165, 710 |
| 71 | 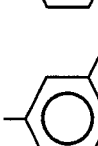 | Me | cis | m.p. 180–182° C. | 2920, 1740, 1620 1600, 1570, 1180 700 |
| 72 | 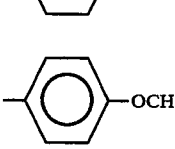 | i-Pr | cis | decomposed at 182° C. | 2970, 1740, 1620 1570, 1510, 1255 1180 |
| 73 | 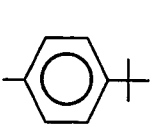 | —CH$_2$C≡CH | cis | m.p. 170–172° C. | 3290, 3090, 2950 1740, 1620, 1470 1180 |
| 74 | 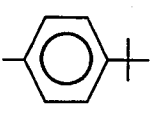 | —CH$_2$CH=CH$_2$ | cis | decomposed at 163° C. | 2960, 1735, 1620 1475, 1180 |
| 75 | 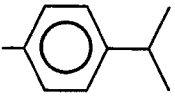 | i-Pr | trans | m.p. 164–166° C. | 2970, 1750, 1620 1600, 1575, 1475 1180, 750 |
| 76 | 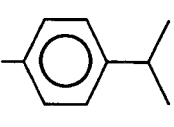 | —CH$_2$CH=CH$_2$ | trans | Viscose Oil | 2960, 1735, 1630 1600, 1580, 1470 1270, 1160, 710 |
| 77 |  | i-Pr | cis | m.p. 175–177° C. | 2980, 1750, 1630 1130, 1160, 1125 1170 |
| 78 | 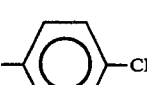 | i-Pr | trans | m.p. 125–127° C. | 3400, 2980, 1710 1620, 1320, 1170 1130, 1065 |
| 79 | 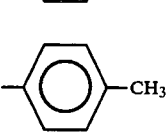 | i-Pr | cis | decomposed at 190° C. | 2980, 1750, 1620 1600, 1570, 1470 1170 |

TABLE 5-continued

| | | | | | |
|---|---|---|---|---|---|
| 80 | [benzodioxole, methyl-substituted] | Me | cis | decomposed at 185° C. | 2980, 1740, 1630 1490, 1260, 1180 1040 |
| 81 | [benzodioxole, methyl-substituted] | Me | trans | decomposed at 181° C. | 2900, 1710, 1650 1500, 1490, 1240 1040, 940, 710 |
| 82 | [dimethylphenyl] | Me | cis | m.p. 195–197° C. | 2910, 1740, 1625 1570, 1180, 680 |
| 83 | [dimethylphenyl] | Me | trans | Viscose Oil | 2920, 1740, 1640 1270, 1175 |
| 84 | [methoxyphenyl, t-Bu substituted] | i-Pr | cis | m.p. 209–211° C. | 2960, 1740, 1620 1570, 1470, 1240 1180, 750, 700 |

| Compound No. | NMR (δ ppm) | Elementary Analysis (%) (calculated values) |
|---|---|---|
| 48 | 2.20(s, 3H), 2.98(s, 3H), 4.62(d, J=6Hz, 1H) 4.96(d, J=6Hz, 1H), 6.70–7.75(m, 7H), 7.85–8.27(m, 1H) (DMSO-d6) | as C18H17NO3 C: 72.96, H: 5.93, N: 5.02 (C: 73.20, H: 5.80, N: 4.74) |
| 49 | 2.20(s, 3H), 3.07(s, 3H), 3.90(s, 1H), 5.18(s, 1H) 6.76–7.12(m, 8H), 7.87–8.30(m, 1H) (CDCl3) | as C18H17NO3 C: 72.93, H: 5.80, N: 4.38 (C: 73.20, H: 5.80, N: 4.74) |
| 50 | 1.20(t, J=7Hz, 3H), 2.58(q, J=7Hz, 2H), 2.97(s, 3H) 4.80(d, J=6Hz, 1H), 5.16(d, J=6Hz, 1H), 6.92–7.20(m, 4H) 7.43–7.67(m, 3H), 8.02–8.14(m, 1H) (DMSO-d6) | as C19H19NO3 C: 74.15, H: 6.28, N: 4.81 (C: 73.76, H: 6.19, N: 4.52) |
| 51 | 1.19(t, J=7Hz, 3H), 2.58(q, J=7Hz, 2H), 3.06(s, 3H) 4.18(s, 1H), 5.34(s, 1H), 6.92–7.63(m, 7H) 7.92–8.03(m, 1H) (DMSO-d6) | as C19H19NO3 C: 73.98, H: 6.28, N: 4.81 (C: 73.76, H: 6.19, N: 4.52) |
| 52 | 1.10(d, J=7Hz, 6H), 2.90(s, 3H), 4.72(d, J=6Hz, 1H) 5.08(d, J=6Hz, 1H), 6.78–7.64(m, 7H), 7.73–8.18(m, 1H) (DMSO-d6) | as C20H21NO3 C: 74.18, H: 6.63, N: 4.37 (C: 74.28, H: 6.54, N: 4.33) |
| 53 | 1.19(d, J=7Hz, 6H), 2.75–2.93(m, 1H), 3.07(s, 3H) 4.20(s, 1H), 5.35(s, 1H), 6.92–7.62(m, 7H) 7.90–8.03(m, 1H) (DMSO-d6) | as C20H21NO3 C: 73.88, H: 6.57, N: 4.05 (C: 74.28, H: 6.54, N: 4.33) |
| 54 | 0.92(t, J=7Hz, 3H), 1.48–1.72(m, 2H), 2.42–2.61(m, 2H) 2.98(s, 3H), 4.80(d, J=6Hz, 1H), 5.18(d, J=6Hz, 1H) 6.90–7.21(m, 4H), 7.42–7.70(m, 3H), 8.02–8.18(m, 1H) | as C20H21NO3 C: 73.89, H: 6.51, N: 4.34 (C: 74.28, H: 6.54, N: 4.33) |
| 55 | 0.90(t, J=7Hz, 3H), 1.28–1.64(m, 2H), 2.40–2.60(m, 2H) 3.08(s, 3H), 4.19(s, 1H), 5.32(s, 1H), 6.93–7.70(m, 7H) 7.93–8.04(m, 1H) (DMSO-d6) | as C20H21NO3 C: 74.49, H: 6.37, N: 4.09 (C: 74.28, H: 6.54, N: 4.33) |
| 56 | 0.92(t, J=7Hz, 3H), 1.20–1.62(m, 4H), 2.40–2.62(m, 2H) 3.04(s, 3H), 4.07(s, 1H), 5.30(s, 1H), 6.92–7.60(m, 7H) 7.89–8.06(m, 1H) (DMSO-d6) | as C21H23NO3 C: 74.56, H: 6.78, N: 3.86 (C: 74.75, H: 6.87, N: 4.15) |
| 57 | 3.03(s, 3H), 4.72(d, J=6Hz, 1H), 5.10(d, J=6Hz, 1H) 7.00–7.80 (m, 7H), 7.93–8.30 (m, 1H) (CDCl3+DMSO-d6) | as C18H14F3NO3 C: 61.76, H: 4.05, N: 3.80 (C: 61.89, H: 4.03, N: 4.00) |
| 58 | 3.10(s, 3H), 4.23(s, 1H), 5.17(s, 1H), 7.27–7.73(m, 5H) 7.93–8.03 (m, 1H) (DMSO-d6) | as C18H14F3NO3 C: 61.94, H: 3.84, N: 3.98 (C: 61.89, H: 4.03, N: 4.00) |
| 59 | 3.00(s, 3H), 3.67(s, 3H), 4.62(d, J=6Hz, 1H) 4.98(d, J=6Hz, 1H), 6.46–7.80(m, 7H), 7.90–8.40(m, 1H) (CDCl3+DMSO-d6) | as C18H17NO4 C: 69.65, H: 5.31, N: 4.20 (C: 69.44, H: 5.51, N: 4.49) |
| 60 | 3.06(s, 3H), 3.70(s, 3H), 4.13(s, 1H), 5.33(s, 1H) 6.77–7.13(m, 4H), 7.27–7.67(m, 3H), 7.97–8.07(m, 1H) (DMSO-d6) | as C18H17NO4 C: 69.19, H: 5.37, N: 4.12 (C: 69.44, H: 5.50, N: 4.49) |
| 61 | 2.98(s, 3H), 4.63(d, J=6Hz, 1H), 5.03(d, J=6Hz, 1H), 6.77–8.42 (m, 8H) | as C17H14ClNO3 C: 64.65, H: 4.32, N: 4.09 |

TABLE 5-continued

| | | |
|---|---|---|
| | (CDCl3+DMSO-d6) | (C: 64.66, H: 4.46, N: 4.43) |
| 62 | 3.02(s, 3H), 3.83(s, 1H), 5.16(s, 1H), 6.70-7.73(m, 8H) 7.88-8.23(m, 1H) (CDCl3) | as C17H14ClNO3 C: 64.34, H: 4.46, N: 4.76 (C: 64.66, H: 4.46, N: 4.43) |
| 63 | 2.99(s, 3H), 4.82(d, J=6Hz, 1H), 5.22(d, J=6Hz, 1H) 6.95-7.13(m, 2H), 7.42-7.70(m, 5H), 8.03-8.19(m, 1H) (DMSO-d6) | as C17H14BrNO3 C: 56.41, H: 3.92, N: 4.05 (C: 56.68, H: 3.91, N: 3.88) |
| 64 | 3.04(s, 3H), 4.20(s, 1H), 5.37(s, 1H), 7.02-7.18(m, 2H) 7.23-7.68(m, 5H), 7.92-8.03(m, 1H) (DMSO-d6) | as C17H14BrNO3 C: 56.55, H: 4.08, N: 4.15 (C: 56.68, H: 3.91, N: 3.88) |
| 65 | 3.07(s, 3H), 4.13(s, 1H), 5.08(s, 1H), 5.32(s, 1H) 6.82-7.14(m, 4H), 7.23-7.62(m, 8H), 7.92-8.08(m, 1H) (DMSO-d6) | as C24H21NO4 C: 74.59, H: 5.40, N: 3.62 (C: 74.40, H: 5.46, N: 3.61) |
| 66 | 2.95(s, 3H), 4.80(d, J=6Hz, 1H), 5.22(d, J=6Hz, 1H) 6.78-8.26(m, 13H) (DMSO-d6) | as C23H19NO3 C: 77.13, H: 5.36, N: 4.15 (C: 77.29, H: 5.35, N: 3.91) |
| 67 | 3.10(s, 3H), 4.22(s, 1H), 5.41(s, 1H), 7.12-7.73(m, 12H) 7.95-8.06(m, 1H) (DMSO-d6) | as C23H19NO3 C: 76.92, H: 5.54, N: 3.71 (C: 77.29, H: 5.35, N: 3.91) |
| 68 | 2.98(s, 3H), 3.70(s, 3H), 4.82(d, J=6Hz, 1H) (DMSO-d6) 5.17(d, J=6Hz, 1H), 6.58-6.70(m, 2H), 6.86-6.92(m, 1H) 7.16-7.28(m, 1H), 7.44-7.70(m, 3H), 8.03-8.15(m, 1H) | as C18H17NO4 C: 69.72, H: 5.53, N: 4.54 (C: 69.44, H: 5.50, N: 4.49) |
| 69 | 3.00(s, 3H), 4.82(d, J=6Hz, 1H), 5.22(d, J=6Hz, 1H) 6.95-7.12(m, 1H), 7.20-7.70(m, 6H), 8.02-8.18(m, 1H) (DMSO-d6) | as C17H14BrNO3 C: 56.79, H: 3.75, N: 3.93 (C: 56.68, H: 3.91, N: 3.88) |
| 70 | 3.10(s, 3H), 4.23(s, 1H), 5.40(s, 1H), 7.01-7.66(m, 7H) 7.92-8.03(m, 1H) (DMSO-d6) | as C17H14BrNO3 C: 56.71, H: 3.86, N: 3.80 (C: 56.68, H: 3.91, N: 3.88) |
| 71 | 2.23(s, 3H), 3.95(s, 3H), 4.78(d, J=6Hz, 1H) 5.14(d, J=6Hz, 1H), 6.80-7.23(m, 4H), 7.43-7.68(m, 3H) 8.10(d, J=6Hz, 1H) (DMSO-d6) | as C18H17NO3 C: 73.27, H: 5.82, N: 4.49 (C: 73.20, H: 5.80, N: 4.74) |
| 72 | 0.92(d, J=7Hz, 3H), 1.35(d, J=7Hz, 3H), 3.70(s, 3H) 4.64-4.89(m, 2H), 5.21(d, J=6Hz, 1H), 6.70-7.08(m, 4H) 7.42-7.71(m, 3H), 8.03-8.16(m, 1H) (DMSO-d6) | as C20H21NO4 C: 70.53, H: 6.13, N: 4.13 (C: 70.78, H: 6.23, N: 4.12) |
| 73 | 1.28(s, 9H), 3.29-3.33(m, 1H), 3.63(d, J=17Hz, 1H) 4.77(d, J=6Hz, 1H), 4.88(dd, J=3Hz, 17Hz, 1H) 5.38(d, J=6Hz, 1H), 6.98-7.08(m, 2H), 7.27-7.38(m, 2H) 7.50-7.72(m, 3H), 8.07-8.18(m, 1H) (DMSO-d6) | as C23H23NO3 C: 76.58, H: 6.37, N: 3.64 (C: 76.43, H: 6.41, N: 3.87) |
| 74 | 1.22(s, 9H), 3.20-3.42(m, 1H), 4.67-4.85(m, 2H) (DMSO-d6) 5.06(d, J=6Hz, 1H), 5.18-5.40(m, 2H), 5.79-6.00(m, 1H) 6.88-7.03(m, 2H), 7.20-7.77(m, 5H), 8.03-8.18(m, 1H) | as C23H25NO3 C: 75.96, H: 6.89, N: 3.59 (C: 76.00, H: 6.93, N: 3.85) |
| 75 | 0.76-1.52(m, 12H), 2.20-3.10(m, 1H), 4.50-5.30(m, 3H) 6.75-7.68(m, 7H), 7.92-8.35(m, 1H), 8.89-9.58(m, 1H) (DCDl3) | as C22H25NO3 C: 75.42, H: 7.01, N: 4.35 (C: 75.18, H: 7.16, N: 3.98) |
| 76 | 1.12(d, J=7Hz, 6H), 2.48-3.68(m, 2H), 3.97(s, 1H) 4.62-6.25(m, 5H), 6.77-7.70(m, 7H), 7.92-8.32(m, 1H) 9.90-10.25(bs, 1H) (DCDl3) | as C22H23NO3 C: 75.94, H: 6.61, N: 4.01 (C: 75.62, H: 6.63, N: 4.00) |
| 77 | 0.98(d, J=7Hz, 3H), 1.35(d, J=7Hz, 3H), 4.72-4.99(m, 2H) 5.40(d, J=6Hz, 1H), 7.14-7.73(m, 7H), 8.00-8.20(m, 1H) (DMSO-d6) | as C20H18F3NO3 C: 63.75, H: 4.97, N: 3.36 (C: 63.65, H: 4.80, N: 3.71) |
| 78 | 0.90(d, J=7Hz, 3H), 1.28(d, J=7Hz, 3H), 4.19(s, 1H) 4.80-5.02(m, 1H), 5.58(s, 1H), 7.00-7.78(m, 5H) 7.92-8.17(m, 1H) (DMSO-d6) | as C20H18F3NO3 C: 63.28, H: 4.69, N: 4.04 (C: 63.65, H: 4.80, N: 3.71) |
| 79 | 0.86(d, J=7Hz, 3H), 1.33(d, J=7Hz, 3H), 2.21(s, 3H) 4.63-4.90(m, 2H), 5.21(d, J=6Hz, 1H), 6.83-7.12(m, 4H) 7.40-7.67(m, 3H), 8.00-8.13(m, 1H) (DMSO-d6) | as C20H21NO3 C: 74.54, H: 6.55, N: 4.44 (C: 74.28, H: 6.54, N: 4.33) |
| 80 | 2.90(s, 3H), 4.67(d, J=6Hz, 1H), 5.03(d, J=6Hz, 1H) 5.92(s, 2H), 6.31-7.60(m, 6H), 7.78-8.12(m, 1H) (DMSO-d6) | as C18H15NO5 C: 66.72, H: 4.50, N: 4.40 (C: 66.45, H: 4.64, N: 4.30) |
| 81 | 3.08(s, 3H), 3.83(s, 1H), 5.13(s, 1H), 5.80(s, 2H) 6.26-6.80(m, 3H), 6.90-7.52(m, 3H), 7.81-8.20(m, 1H) 10.92-11.30(bs, 1H) (CDCl3+DMSO-d6) | as C18H15NO5 C: 66.36, H: 4.81, N: 4.02 (C: 66.45, H: 4.64, N: 4.30) |
| 82 | 2.26(s, 3H), 2.44(s, 3H), 2.90(s, 3H), 4.70(d, J=6Hz, 1H) 5.45(d, J=6Hz, 1H), 6.86-7.08(m, 3H), 7.20-7.72(m, 3H) 8.03-8.15(m, 1H) (DMSO-d6) | as C19H19NO3 C: 73.82, H: 6.08, N: 4.62 (C: 73.76, H: 6.19, N: 4.52) |
| 83 | 2.23(s, 3H), 2.48(s, 3H), 3.73(s, 3H), 4.03(s, 1H) 5.48(s, 1H), 6.39-6.43(m, 1H), 6.76-6.85(m, 1H) 7.10(s, 1H), 7.20-7.60(m, 3H), 7.95-8.08(m, 1H) (DMSO-d6) | as C19H19NO3 C: 73.47, H: 5.99, N: 4.81 (C: 73.76, H: 6.19, N: 4.52) |
| 84 | 0.62-1.45(m, 15H), 3.73(s, 3H), 4.43-5.18(m, 2H) 5.70(d, J=6Hz, 1H), 6.47-6.88(m, 2H), 7.07-7.58(m, 4H) 7.92-8.30(m, 1H), 9.90(bs, 1H) (DCDl3) | as C24H29NO4 C: 73.04, H: 7.41, N: 3.56 (C: 72.88, H: 7.39, N: 3.54) |

TABLE 6
| Compound No. | R8/R9/R10/R11/R12 structure | R7 | Physical Properties | IR (KBr, cm−1) |
|---|---|---|---|---|
| 86 | 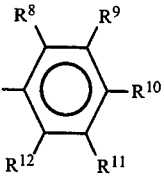 —C6H4—CH3 | Me | m.p. 117–118° C. | 3030, 2910, 1640 1600, 1480, 1460 1390, 1260, 820 740, 700 |
| 87 | 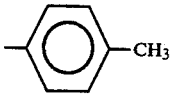 —C6H4—Et | Me | m.p. 71–73° C. | 2960, 1650, 1470 1260, 830, 745 |
| 88 | 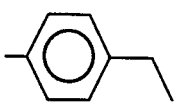 —C6H4—iPr | Me | $n_D^{27.1}$ = 1.5866 | 2950, 1640, 1600 1470, 1390, 1260 825, 740 (NaCl) |
| 89 | 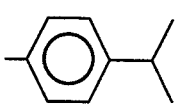 —C6H4—nPr | Me | $n_D^{27.1}$ = 1.5810 | 2950, 2930, 1740 1650, 1605, 1470 1395, 1265, 1100 740, 700 (NaCl) |
| 90 | 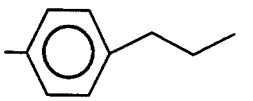 —C6H4—nBu | Me | $n_D^{27.1}$ = 1.5729 | 2950, 2920, 1740 1650, 1470, 1265 1100, 740 (NaCl) |
| 91 | 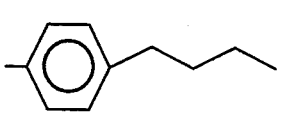 —C6H4—n-hexyl | Me | $n_D^{26.9}$ = 1.5618 | 2930, 2850, 1740 1650, 1470, 1400 1265, 740 (NaCl) |
| 92 | 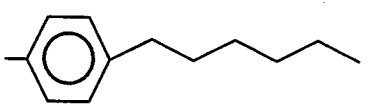 —C6H4—CF3 | Me | m.p. 97–98° C. | 3070, 2900, 1650 1605, 1470, 1400 1325, 1265, 1160 1120, 825, 735 |
| 93 | 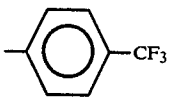 —C6H4—N(CH3)2 | Me | m.p. 110–112° C. | 2900, 1645, 1520 1345, 1265, 820 740 |
| 94 | 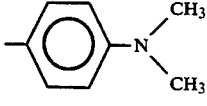 —C6H4—Cl | Me | m.p. 120–121° C. | 3090, 2950, 2900 1650, 1490, 1470 1395, 1265, 1100 830, 740 |
| 95 | 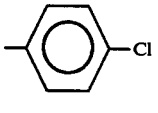 —C6H4—Br | Me | m.p. 145–146° C. | 3090, 2950, 2900 1650, 1605, 1490 1390, 1340, 1265 1050, 830, 735 |
| 96 | 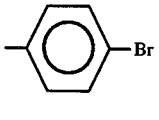 —C6H4—C6H5 | Me | m.p. 159–160° C. | 3020, 1640, 1600 1575, 1480, 1390 1260, 740, 695 |
| 97 | 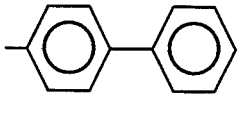 —C6H4—OCH3 | Me | m.p. 73–74° C. | 2950, 2900, 1740 1650, 1610, 1580 1470, 1400, 1250 1180, 830, 745 |

TABLE 6-continued
| # | Structure | R | m.p. / n | IR |
|---|---|---|---|---|
| 98 | 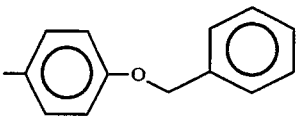 | Me | m.p. 116–118° C. | 2940, 2890, 1645 1380, 1240, 1010 745, 700 |
| 99 | 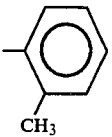 | Me | m.p. 99–101° C. | 2880, 1640, 1600 1390, 1325, 1260 740 |
| 100 | 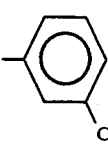 | Me | m.p. 51–53° C. | 2920, 1640, 1600 1475, 1330, 1260 740 |
| 101 | 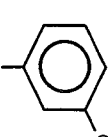 | Me | m.p. 80–84° C. | 2960, 2910, 1650 1610, 1580, 1325 1270, 1260, 1050 740, 725 |
| 102 | 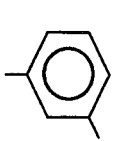 | Me | m.p. 133–135° C. | 3060, 2900, 1645 1470, 1390, 1260 790, 740, 690 |
| 103 | 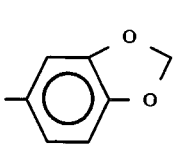 | Me | m.p. 100–101° C. | 2900, 1640, 1490 1440, 1255, 1035 820, 735 |
| 104 | 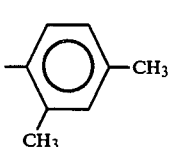 | Me | $n_D^{25.0}$ = 1.5852 | 3000, 2920, 1650 1480, 1400, 1270 755 |
| 105 | 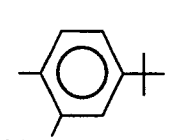 | Me | m.p. 126–128° C. | 2950, 1650, 1460 1230, 735 |
| 106 | 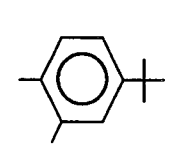 | i-Pr | m.p. 134–135° C. | 2960, 1640, 1460 1240, 1030, 730 |
| 107 | 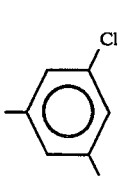 | Me | m.p. 178–180° C. | 3070, 1650, 1575 1480, 1325, 800 740 |

TABLE 6-continued
| | | | | |
|---|---|---|---|---|
| 108 | 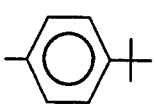 | Et | $n_D^{27.1} = 1.5689$ | 2960, 1650, 1470 1305, 1270, 1110 830, 740 (NaCl) |
| 109 | 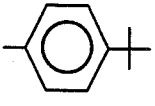 | i-Pr | m.p. 107–108° C. | 2975, 1645, 1460 1430, 1325, 1260 1180, 820, 735 |
| 110 | 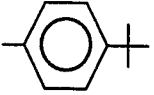 | —CH$_2$C≡CH | $n_D^{27.1} = 1.5812$ | 3300, 2960, 2130 1660, 1605, 1580 1465, 1260, 1160 830, 740 (NaCl) |
| 111 | 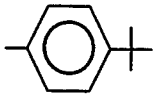 | —CH$_2$CH=CH$_2$ | $n_D^{27.1} = 1.5664$ | 2950, 1740, 1650 1600, 1465, 1405 1260, 1160, 825 740 (NaCl) |
| 112 | 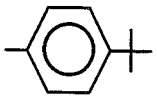 | t-Bu | m.p. 147–150° C. | 2950, 1645, 1400 1330, 1200, 825 735 |
| 113 | 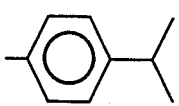 | i-Pr | m.p. 95–97° C. | 2970, 1635, 1465 1420, 1180, 830 750, 735 |
| 114 | 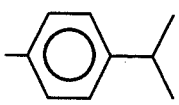 | —CH$_2$CH=CH$_2$ | $n_D^{25.0} = 1.5831$ | 2960, 1650, 1470 1415, 1265, 740 (NaCl) |
| 115 | 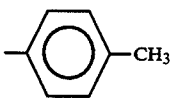 | i-Pr | m.p. 89–91° C. | 2980, 1640, 1470 1320, 1180, 820 735 |
| 116 | 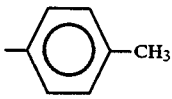 | t-Bu | m.p. 137–141° C. | 2950, 1640, 1400 1330, 1200, 820 |
| 117 | 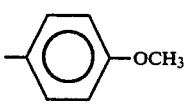 | —CH$_2$CH=CH$_2$ | $n_D^{25.0} = 1.5969$ | 1650, 1510, 1470 1250, 750 (NaCl) |
| 118 | 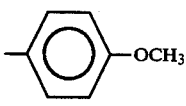 | i-Pr | $n_D^{27.1} = 1.5763$ | 2970, 2830, 1740 1640, 1510, 1465 1250, 1180, 830 745 (NaCl) |
| 119 | 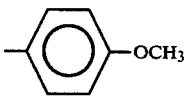 | —CH$_2$C≡CH | Viscose Product | 3280, 2950, 2110 1640, 1600, 1580 1460, 1250, 1180 825, 740 (NaCl) |
| 120 | 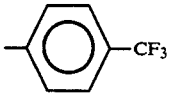 | i-Pr | $n_D^{27.0} = 1.5396$ | 2970, 1735, 1650 1600, 1575, 1460 1320, 1160, 830 735 (NaCl) |

TABLE 6-continued

| | | | | |
|---|---|---|---|---|
| 121 | 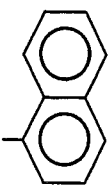 | Me | m.p. 108–111° C. | 3530, 1640, 1600 1575, 1480, 1270 780, 735 |
| 122 | 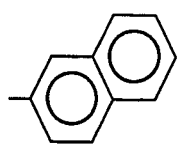 | Me | m.p. 123–124° C. | 3050, 1645, 1600 1475, 1260, 820 740 |
| 123 | 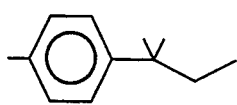 | Me | m.p. 106–107° C. | 2960, 1650, 1470 1395, 1265, 740 (KBr) |
| 124 | 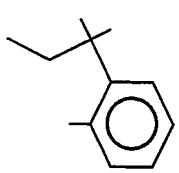 | Me | $n_D^{29.7}$ = 1.5619 | 2960, 1740, 1650 1480, 1400, 1260 740 (NaCl) |

| Compound No. | NMR (δ ppm) | Elementary Analysis (%) (calculated values) |
|---|---|---|
| 86 | 2.20(s, 3H), 2.70–3.30(m, 4H), 3.58(d, J=7Hz, 16Hz, 1H) 4.67(dd, J=3Hz, 7Hz, 1H), 6.70–7.53(m, 7H) 7.85–8.25(m, 1H) (CDCl3) | as C17H17NO C: 81.08, H: 6.62, N: 5.91 (C: 81.24, H: 6.81, N: 5.57) |
| 87 | 1.15(t, J=7Hz, 3H), 2.30–3.25(m, 6H) 3.65(dd, J=7Hz, 16Hz, 1H), 4.73(dd, J=3Hz, 7Hz, 1H) 6.80–7.50(m, 7H), 7.95–8.25(m, 1H) (CDCl3) | as C18H19NO C: 81.33, H: 7.18, N: 5.28 (C: 81.47, H: 7.21, N: 5.27) |
| 88 | 1.16(t, J=7Hz, 6H), 2.55–3.25(m, 5H) 3.60(dd, J=7Hz, 16Hz, 1H), 4.70(dd, J=3Hz, 7Hz, 1H) 6.80–7.42(m, 7H), 7.92–8.23(m, 1H) (CDCl3) | as C19H21NO C: 81.96, H: 7.60, N: 5.16 (C: 81.68, H: 7.57, N: 5.01) |
| 89 | 0.86(t, J=7Hz, 3H), 1.44–1.90(m, 2H), 2.26–3.25(m, 6H) 3.62(dd, J=7Hz, 16Hz, 1H), 4.72(dd, J=3Hz, 7Hz, 1H) 6.80–7.40(m, 7H), 7.90–8.22(m, 1H) (CDCl3) | as C19H21NO C: 81.57, H: 7.64, N: 5.14 (C: 81.68, H: 7.57, N: 5.01) |
| 90 | 0.65–1.82(m, 7H), 2.22–3.24(m, 6H) 3.60(dd, J=7Hz, 16Hz, 1H), 4.68(dd, J=3Hz, 7Hz, 1H) 6.80–7.42(m, 7H), 7.85–8.20(m, 1H) (CDCl3) | as C20H23NO C: 82.03, H: 7.93, N: 4.80 (C: 81.87, H: 7.90, N: 4.77) |
| 91 | 0.60–1.88(m, 11H), 2.27–2.70(m, 2H), 2.73–3.25(m, 4H) 3.62(dd, J=7Hz, 16Hz, 1H), 4.20(dd, J=3Hz, 7Hz, 1H) 6.72–7.43(m, 7H), 7.84–8.27(m, 1H) (CDCl3) | as C22H27NO C: 82.52, H: 8.44, N: 4.62 (C: 82.20, H: 8.46, N: 4.35) |
| 92 | 2.65–3.35(m, 4H), 3.64(dd, J=7Hz, 16Hz, 1H) 4.74(dd, J=3Hz, 7Hz, 1H) 6.70–7.74(m, 7H), 7.80–8.30(m, 1H) (CDCl3) | as C17H14F3NO C: 66.59, H: 4.69, N: 4.66 (C: 66.88, H: 4.62, N: 4.58) |
| 93 | 2.70–3.82(m, 11H), 4.60(dd, J=3Hz, 7Hz, 1H) 6.32–7.47 (m, 7H), 7.87–8.22 (m, 1H) (CDCl3) | as C18H20N2O C: 77.03, H: 7.06, N: 10.27 (C: 77.11, H: 7.18, N: 9.99) |
| 94 | 2.72–3.23(m, 4H), 3.69(dd, J=7Hz, 16Hz, 1H) 4.72(dd, J=3Hz, 7Hz, 1H) 6.80–7.45(m, 7H), 7.90–8.25(m, 1H) (CDCl3) | as C16H14NO C: 70.37, H: 5.20, N: 5.31 (C: 70.71, H: 5.19, N: 5.15) |
| 95 | 2.70–3.20(m, 4H), 3.77(dd, J=7Hz, 16Hz, 1H) 4.72(dd, J=3Hz, 7Hz, 1H) 6.75–7.45(m, 7H), 7.92–8.24(m, 1H) (CDCl3) | as C16H14BrNO C: 60.43, H: 4.45, N: 4.46 (C: 60.77, H: 4.46, N: 4.42) |
| 96 | 2.77–3.26(m, 4H), 3.66(dd, J=7Hz, 16Hz, 1H) 4.77(dd, J=3Hz, 7Hz, 1H) 6.67–7.65(m, 12H), 7.90–8.27(m, 1H) (CDCl3) | as C22H19NO C: 84.28, H: 6.10, N: 4.34 (C: 84.31, H: 6.11, N: 4.46) |
| 97 | 2.67–3.10(m, 4H), 3.30–3.82(m, 4H) 4.66(dd, J=3Hz, 7Hz, 1H) 6.52–7.40(m, 7H), 7.88–8.20(m, 1H) (CDCl3) | as C17H17NO2 C: 76.37, H: 6.24, N: 5.26 (C: 76.38, H: 6.40, N: 5.23) |
| 98 | 2.90–3.18(m, 4H), 3.62(dd, J=7Hz, 16Hz, 1H) 4.72(dd, J=3Hz, 7Hz, 1H), 4.98(s, 2H), 6.75–7.50(m, 4H) 7.22–7.48(m, 8H), 8.08–8.20(m, 1H) (CDCl3) | as C23H21NO2 C: 80.58, H: 6.21, N: 3.90 (C: 80.44, H: 6.16, N: 4.07) |
| 99 | 2.40(s, 3H), 2.70–3.12(m, 4H) | as C17H17NO |

| | | |
|---|---|---|
| | 3.60(dd, J=7Hz, 16Hz, 1H), 4.98(dd, J=3Hz, 7Hz, 1H)<br>6.70–7.42(m, 7H), 8.00–8.28(m, 1H) (CDCl3) | C: 81.56, H: 6.62, N: 5.43<br>(C: 81.24, H: 6.81, N: 5.57) |
| 100 | 2.20(s, 3H), 2.69–3.20(m, 4H)<br>3.60(dd, J=7Hz, 16Hz, 1H), 4.67(dd, J=3Hz, 7Hz, 1H)<br>6.65–7.39(m, 7H), 7.86–8.20(m, 1H) (CDCl3) | as C17H17NO<br>C: 81.45, H: 6.98, N: 5.57<br>(C: 81.24, H: 6.81, N: 5.57) |
| 101 | 2.78–3.20(m, 4H), 3.38–3.86(m, 4H),<br>3.69(dd, J=3Hz, 7Hz, 1H)<br>6.40–7.43(m, 7H), 7.85–8.16(m, 1H)<br>(CDCl3) | as C17H17NO2<br>C: 76.02, H: 6.39, N: 5.62<br>(C: 76.38, H: 6.40, N: 5.23) |
| 102 | 2.72–3.20(m, 4H), 3.65(dd, J=7Hz, 16Hz, 1H)<br>4.70(dd, J=3Hz, 7Hz, 1H)<br>6.72–7.42(m, 7H), 7.90–8.20(m, 1H) (CDCl3) | as C16H14BrNO<br>C: 60.70, H: 4.47, N: 4.79<br>(C: 60.77, H: 4.46, N: 4.42) |
| 103 | 2.72–3.18(m, 4H), 3.58(dd, J=7Hz, 16Hz, 1H)<br>4.63(dd, J=3Hz, 7Hz, 1H), 5.80(s, 2H)<br>6.32–7.52(m, 6H), 7.86–8.22(m, 1H), | as C17H15NO3<br>C: 72.89, H: 5.53, N: 4.62<br>(C: 72.58, H: 5.37, N: 4.97) |
| 104 | 2.12(s, 3H), 2.33(s, 3H), 2.60–3.78(m, 5H)<br>4.90(dd, J=3Hz, 7Hz, 1H)<br>6.40–7.34(m, 6H), 7.85–8.22(m, 1H) (CDCl3) | as C18H19NO<br>C: 81.11, H: 7.39, N: 5.54<br>(C: 81.47, H: 7.21, N: 5.27) |
| 105 | 1.23(s, 9H), 2.85–3.74(s, 5H), 3.92(s, 3H)<br>5.13(dd, J=3Hz, 7Hz, 1H)<br>6.60–7.40(m, 6H), 7.90–8.25(m, 1H) (CDCl3) | as C21H25NO2<br>C: 78.23, H: 7.74, N: 4.69<br>(C: 77.98, H: 7.79, N: 4.33) |
| 106 | 0.89(d, J=7Hz, 3H), 1.22(s, 9H), 1.32(d, J=7Hz, 3H)<br>3.02(d, J=16Hz, 1H), 3.43(dd, J=7Hz, 16Hz, 1H), 3.92(s, 3H)<br>4.97–5.10(m, 1H), 5.28(d, J=7Hz, 1H), 6.58–6.98(m, 4H)<br>7.20–7.36(m, 2H), 8.08–8.15(m, 1H) (CDCl3) | as C23H29NO2<br>C: 78.84, H: 8.17, N: 3.70<br>(C: 78.59, H: 8.31, N: 3.98) |
| 107 | 2.83–3.95(m, 5H)<br>5.06(dd, J=3Hz, 7Hz, 1H)<br>6.86–7.58(m, 6H), 7.73–8.08(m, 1H) (CDCl3) | as C16H13Cl2NO<br>C: 62.61, H: 4.07, N: 4.56<br>(C: 62.76, H: 4.27, N: 4.57) |
| 108 | 1.00–1.36(m, 12H), 2.62–4.42(m, 4H)<br>4.85(dd, J=3Hz, 7Hz, 1H)<br>6.75–7.42(m, 7H), 7.95–8.32(m, 1H) (CDCl3) | as C21H25NO<br>C: 81.88, H: 8.14, N: 4.31<br>(C: 82.04, H: 8.19, N: 4.55) |
| 109 | 0.82–1.46(m, 15H), 2.92(dd, J=3Hz, 16Hz, 1H)<br>3.60(dd, J=7Hz, 16Hz, 1H), 4.89(dd, J=3Hz, 7Hz, 1H)<br>6.78–7.42(m, 7H), 7.98–8.20(m, 1H) (CDCl3) | as C22H27NO<br>C: 81.99, H: 8.34, N: 4.48<br>(C: 82.20, H: 8.46, N: 4.35) |
| 110 | 1.23(s, 9H), 2.18(t, J=2Hz, 1H), 2.80–3.90(m, 3H)<br>4.96–5.38(m, 2H), 6.83–7.48(m, 7H), 7.96–8.20(m, 1H)<br>(CDCl3) | as C22H23NO<br>C: 83.17, H: 7.17, N: 4.28<br>(C: 83.24, H: 7.30, N: 4.41) |
| 111 | 1.23(s, 9H), 2.75–3.82(m, 3H)<br>4.62–5.37(m, 4H), 5.50–6.18(m, 1H)<br>6.77–7.42(m, 7H), 7.93–8.23(m, 1H)<br>(CDCl3) | as C22H25NO<br>C: 82.52, H: 7.76, N: 4.23<br>(C: 82.71, H: 7.88, N: 4.38) |
| 112 | 1.20(s, 9H), 1.50(s, 9H), 2.82(dd, J=3Hz, 16Hz, 1H)<br>3.58(dd, J=7Hz, 16Hz, 1H), 5.18(dd, J=3Hz, 7Hz, 1H)<br>6.80–7.32(m, 7H), 7.89–8.20(m, 1H) (CDCl3) | as C23H29NO<br>C: 82.04, H: 8.67, N: 4.45<br>(C: 82.34, H: 8.71, N: 4.17) |
| 113 | 0.72–1.47(m, 12H), 2.50–3.18(m, 2H)<br>3.58(dd, J=7Hz, 16Hz, 1H), 4.73–5.38(m, 2H)<br>6.70–7.48(m, 7H), 7.92–8.30(m, 1H) (CDCl3) | as C21H25NO<br>C: 82.10, H: 8.14, N: 4.94<br>(C: 82.04, H: 8.19, N: 4.55) |
| 114 | 1.15(d, J=7Hz, 6H), 2.50–3.90(m, 41H), 4.62–6.18(m, 5H)<br>6.78–7.60(m, 7H), 7.92–8.28(m, 1H)<br>(CDCl3) | as C21H23NO<br>C: 82.21, H: 7.39, N: 4.43<br>(C: 82.58, H: 7.59, N: 4.58) |
| 115 | 0.92(d, J=7Hz, 3H), 1.28(d, J=7Hz, 3H), 2.17(s, 3H) (CDCl3)<br>2.86(dd, J=3Hz, 16Hz, 1H), 3.55(dd, J=7Hz, 16Hz, 1H)<br>4.72–5.33(m, 2H), 6.68–7.40(m, 7H), 7.90–8.25(m, 1H) | as C19H21NO<br>C: 81.28, H: 7.47, N: 4.61<br>(C: 81.68, H: 7.57, N: 5.01) |
| 116 | 1.48(s, 9H), 2.21(s, 3H), 2.91(d, J=16Hz, 1H)<br>3.62(dd, J=6Hz, 16Hz, 1H), 5.24(d, J=6Hz, 1H)<br>6.82–7.28(m, 7H), 8.03–8.08(m, 1H) (CDCl3) | as C20H23NO<br>C: 81.79, H: 8.00, N: 5.11<br>(C: 81.87, H: 7.90, N: 4.77) |
| 117 | 2.68–3.87(m, 6H), 4.50–6.20(m, 5H)<br>6.50–7.48(m, 7H), 7.90–8.23(m, 1H)<br>(CDCl3) | as C19H19NO2<br>C: 77.95, H: 6.63, N: 4.84<br>(C: 77.79, H: 6.52, N: 4.77) |
| 118 | 0.90(d, J=7Hz, 3H), 1.27(d, J=7Hz, 3H)<br>2.78(dd, J=3Hz, 16Hz, 1H), 3.20–3.72(m, 4H)<br>4.60–5.25(m, 2H), 6.40–7.32(m, 7H), 7.82–8.14(m, 1H)<br>(CDCl3) | as C19H21NO2<br>C: 77.43, H: 7.31, N: 4.76<br>(C: 77.26, H: 7.16, N: 4.74) |
| 119 | 2.17(t, J=2Hz, 1H), 2.69–3.82(m, 6H)<br>4.87–5.30(m, 2H), 6.52–7.70(m, 7H)<br>7.85–8.15(m, 1H)<br>(CDCl3) | as C19H17NO2<br>C: 78.11, H: 5.82, N: 4.49<br>(C: 78.32, H: 5.88, N: 4.80) |
| 120 | 0.91(d, J=7Hz, 3H), 1.32(d, J=7Hz, 3H), 2.96(d, J=16Hz, 1H)<br>3.63(dd, J=6Hz, 16Hz, 1H), 4.99(d, J=6Hz, 1H)<br>5.14(m, 1H), 6.85–6.98(m, 1H), 7.12–7.51(m, 6H)<br>8.07–8.20(m, 1H) (CDCl3) | as C19H18F3NO<br>C: 68.09, H: 5.30, N: 4.40<br>(C: 68.45, H: 5.44, N: 4.20) |
| 121 | 3.02–3.42(m, 4H), 3.82(dd, J=7Hz, 16Hz, 1H)<br>5.58(dd, J=3Hz, 7Hz, 1H)<br>6.62–8.32(m, 11H) (CDCl3) | as C20H17NO<br>C: 83.23, H: 5.94, N: 4.74<br>(C: 83.59, H: 5.96, N: 4.87) |
| 122 | 2.85–3.30(m, 4H), 3.68(dd, J=7Hz, 16Hz, 1H)<br>4.88(dd, J=3Hz, 7Hz, 1H)<br>6.70–7.85(m, 10H), 7.90–8.28(m, 1H) (CDCl3) | as C20H17NO<br>C: 83.28, H: 5.91, N: 4.58<br>(C: 83.59, H: 5.96, N: 4.87) |
| 123 | 0.63(t, J=7Hz, 3H), 1.22(s, 3H), 1.58(q, J=7Hz, 2H)<br>2.98–3.15(m, 4H), 3.65(dd, J=16Hz, 7Hz, 1H)<br>4.74(dd, J=7Hz, 3Hz, 1H), 6.96–7.06(m, 3H)<br>7.20(d, J=8Hz, 2H), 7.29–7.40(m, 2H), 8.12–8.19(m, 1H)<br>(CDCl3) | as C21H25NO<br>C: 81.80, H: 8.29, N: 4.29<br>(C: 82.04, H: 8.20, N: 4.56) |

TABLE 6-continued

| 124 | 0.52(t, J=7Hz, 3H), 1.14–1.24(m, 6H), 1.51(q, J=7Hz, 2H) 2.96–3.16(m, 4H), 3.65(dd, J=17Hz, 7Hz, 1H) 4.75(dd, J=7Hz, 3Hz, 1H), 6.85–7.08(m, 3H) 7.14–7.42(m, 4H), 8.11–8.24(m, 1H) (CDCl3) | as C21H25NO C: 82.10, H: 8.06, N: 4.39 (C: 82.04, H: 8.20, N: 4.56) |
|---|---|---|

TABLE 7

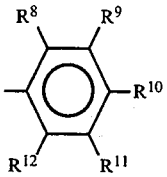

| Compound No. | | R7 | Physical Properties | IR (KBr, cm−1) |
|---|---|---|---|---|
| 127 | 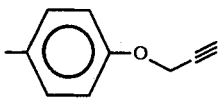 | Me | m.p. 87–88° C. | 3220, 2120, 1640 1510, 1240, 1020 830, 755, 735 |
| 128 | 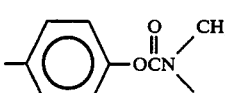 | Me | m.p. 167–169° C. | 1715, 1645, 1390 1210, 1170, 725 |
| 129 | 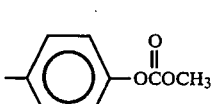 | Me | m.p. 105–108° C. | 1755, 1650, 1440 1270, 1225, 940 |

| Compound No. | NMR (δ ppm) | Elementary Analysis (%) (calculated value) |
|---|---|---|
| 127 | 2.46(d, J=2Hz, 1H), 2.77–3.20(m, 4H) 3.60(dd, J=7Hz, 16Hz, 1H)), 4.50–4.85(m, 2H) 6.68–7.48(m, 7H), 7.92–8.20(m, 1H) (CDCl3) | as C19H17NO2 C: 78.63, H: 5.77, N: 4.50 (C: 78.32, H: 5.88, N: 4.80) |
| 128 | 2.80–3.23(m, 10H), 3.68(dd, J=7Hz, 16Hz, 1H) 4.78(dd, J=3Hz, 7Hz, 1H) 6.83–7.75(m, 7H), 8.00–8.22(m, 1H) (CDCl3) | as C19H20N2O3 C: 70.18, H: 6.23, N: 8.75 (C: 70.35, H: 6.21, N: 8.63) |
| 129 | 2.68–3.22(m, 4H), 3.44–3.95(m, 4H) 4.78(dd, J=3Hz, 7Hz, 1H), 6.80–7.42(m, 7H) 7.90–8.23(m, 1H) (CDCl3) | as C18H17NO4 C: 69.58, H: 5.55, N: 4.84 (C: 69.44, H: 5.50, N: 4.49) |

We claim:

1. A fungicide composition comprising a fungicidally effective amount of a compound of formula [I] and acid addition salts thereof:

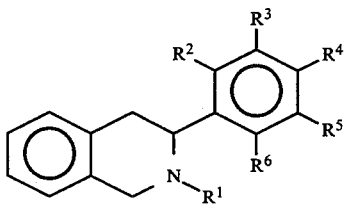

[I]

wherein $R^1$ represents $C_1$–$C_5$ linear or branched alkyl, $C_2$–$C_5$ linear or branched alkenyl, $C_2$–$C_5$ linear or branched alkynyl; $R^2$, $R^3$, $R^4$, $R^5$ and $R^6$, the same or different, represent hydrogen, $C_1$–$C_{10}$ linear or branched alkyl, $C_3$–$C_{10}$ linear or branched alkenyl, $C_2$–$C_{10}$ linear or branched alkynyl, $C_1$–$C_{10}$ linear or branched alkoxy, $C_2$–$C_{10}$ linear or branched alkenyloxy, $C_2$–$C_{10}$ linear or branched alkynyloxy, benzyloxy, hydroxy, haloalkyl, amino, mono- or di-substituted amino substituted with $C_1$–$C_4$ linear or branched alkyl, phenyl or halogen; $R^2$ and $R^3$ may be bonded through a group of the formula —O-(-CH$_2$)$_m$O— wherein m represents an integer of 1 or 2 or -(-CH=CH)$_2$ to form a ring;

and $R^4$ and $R^5$ may be bonded through a group of the formula —O-(-CH$_2$)$_m$O— wherein m represents an integer of 1 or 2 or -(-CH=CH)$_2$ to form a ring.

2. A method of controlling fungal disease on plants comprising applying to the plants a fungicidally effective amount of a compound of formula [I] and acid addition salts thereof:

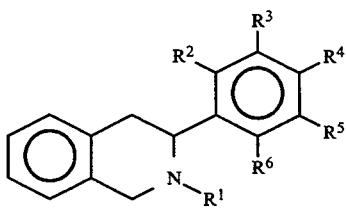

[I]

wherein $R^1$ represents $C_1$–$C_5$ linear or branched alkyl, $C_2$–$C_5$ linear or branched alkenyl, $C_2$–$C_5$ linear or branched alkynyl; $R^2$ $R^3$ $R^4$ $R^5$ and $R^6$ the same or different, represent hydrogen, $C_1$–$C_{10}$ linear or branched alkyl, $C_3$–$C_{10}$ linear or branched alkenyl, $C_2$–$C_{10}$ linear or branched alkynyl, $C_1$–$C_{10}$ linear or branched alkoxy, $C_2$–$C_{10}$ linear or branched alkenyloxy, $C_2$–$C_{10}$ linear or branched alkynyloxy, benzyloxy, hydroxy, haloalkyl, amino, mono- or di-substituted amino substituted with $C_1$–$C_4$ linear or branched alkyl, phenyl or halogen; $R^2$ and $R^3$ may be bonded through a group of the formula —O—$(CH_2)_m$— wherein m represents an integer of 1 or 2 or —$(CH=CH)_2$ to form a ring; and $R^4$ and $R^5$ may be bonded through a group of the formula —O—$(CH_2)_m$O— wherein m represents an integer of 1 or 2 or —$(CH=CH)_2$ to form a ring.

3. A method of controlling fungal disease on plants comprising applying a fungicidally effective amount of the composition of claim 1 to the plants.

* * * * *